US008389478B2

(12) United States Patent
Dewji et al.

(10) Patent No.: US 8,389,478 B2
(45) Date of Patent: Mar. 5, 2013

(54) METHODS AND COMPOSITIONS FOR TREATING NEURODEGENERATIVE DISORDERS AND ALZHEIMER'S DISEASE AND IMPROVING NORMAL MEMORY

(75) Inventors: Nazneen Dewji, San Diego, CA (US); S. Jonathan Singer, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 75 days.

(21) Appl. No.: 12/966,969

(22) Filed: Dec. 13, 2010

(65) Prior Publication Data

US 2011/0201557 A1 Aug. 18, 2011

Related U.S. Application Data

(63) Continuation of application No. 11/693,926, filed on Mar. 30, 2007, now Pat. No. 7,851,228.

(60) Provisional application No. 60/788,524, filed on Mar. 31, 2006.

(51) Int. Cl.
*A61K 38/00* (2006.01)
*C07K 14/72* (2006.01)

(52) U.S. Cl. ..................... 514/17.8; 514/20.6
(58) Field of Classification Search .......... None
See application file for complete search history.

(56) References Cited

U.S. PATENT DOCUMENTS

| | | | |
|---|---|---|---|
| 7,851,228 | B2 | 12/2010 | Dewji et al. |
| 2002/0015939 | A1 | 2/2002 | McCarthy et al. |
| 2002/0016978 | A1 | 2/2002 | Zheng et al. |
| 2002/0064828 | A1 | 5/2002 | Monteiro et al. |
| 2002/0082211 | A1 | 6/2002 | Arvizu |
| 2002/0086444 | A1 | 7/2002 | Tanzi |
| 2003/0059938 | A1 | 3/2003 | Annaert |
| 2003/0065141 | A1 | 4/2003 | Carter |
| 2003/0113811 | A1 | 6/2003 | Hale |
| 2003/0175278 | A1 | 9/2003 | Monteiro |
| 2004/0143860 | A1 | 7/2004 | St. George-Hyslop |
| 2004/0154047 | A1 | 8/2004 | Scott |
| 2004/0205836 | A1 | 10/2004 | Shen |
| 2004/0265891 | A1 | 12/2004 | Arvizu |
| 2004/0267004 | A1 | 12/2004 | Tohyama |
| 2005/0101766 | A1 | 5/2005 | Blackstock |
| 2005/0214837 | A1 | 9/2005 | St. George-Hyslop |
| 2005/0288212 | A1 | 12/2005 | Hale |
| 2009/0305946 | A1 | 12/2009 | Dewji et al. |

FOREIGN PATENT DOCUMENTS

| | | |
|---|---|---|
| EP | 1967527 A1 | 9/2008 |
| WO | 2007092861 A2 | 8/2007 |
| WO | 2007123680 A3 | 11/2007 |
| WO | 2010132609 A3 | 11/2010 |

OTHER PUBLICATIONS

Georgakopoulos, Anastasios, "Metalloproteinase/Presenilin1 processing of ephrinB regulates EphB-induced Src phosphorylation and sigaling", The EMBO Journal, 2006, vol. 25, pp. 1242-1252.

Ulm, John D., Transmittal of International Search Report and Written Opinion, International Search Report, and Written Opinion, PCT/US07/07908, Aug. 25, 2008.

Dewji, Nazneen N., "Specific intercellular binding of the beta-amyloid precursor protein to the presenilins induces intercellular signaling: its significance for Alzheimer's disease." Proc Natl Acad Sci USA, 1998, 95(25), pp. 15055-15060.

Dewji, Nazneen N., "The structure and functions of the presenilins." Cell Mol Life Sci, 2005, 62(10), pp. 1109-1119. Review.

Dewji, Nazneen N., "Presenilin structure in mechanisms leading to Alzheimer's disease." J Alzheimers Dis., 2006, 10 (2-3), pp. 277-290. Review.

Dewji, et al., "An early specific cell-cell interaction occurs in the production of B-amyloid in cell cultures," Proceedings of the National Academy of Sciences, 2006, pp. 1540-1545, vol. 103, No. 5.

Lunter, Pim, Supplementary European Search Report, Date of Completion of Search: Mar. 4, 2009, European Patent Application No. EP07754428.

Gandy, Sam; M. K. Doeven; and B. Poolman; "Alzheimer disease: presenilin springs a leak" Nature Medicine; Oct. 2006, vol. 12, No. 10, pp. 1121-1123.

Saura, Carlos A.; G. Chen; S. Malkani; S-Y Choi; R. H. Takahashi; D. Zhang; G. K. Gouras; A. Kirkwood; R. G. M. Morris; and J. Shen "Conditional Inactivation of Presenilin 1 Prevents Amyloid Accumulation and Temporarily Rescues Contextual and Spatial Working Memory Impairments in Amyloid Precursor Protein Transgenic Mice" The Journal of Neuroscience; Jul. 20, 2005; vol. 25, No. 29, pp. 6755-6764.

Beglopoulos, Vassilios; X. Sun; C. A. Saura, C. A. Lemere; R. D. Kim; and J. Shen; The Journal of Biological Chemistry Nov. 5, 2004; vol. 279, No. 45, pp. 46907-46914.

Cervantes, Sara; C. A. Saura; E. Pomares; R. Gonzales-Duarte; "Functional Implications of the Presenilin Dimerization" The Journal of Biological Chemistry, Aug. 27, 2004, vol. 279, No. 35. pp. 36519-36529.

Saura, Carlos A.; S-Y Choi; V. Beglopoulos; S. Maikani; D. Zhang; B. S. Shankaranarayana Roa; S. Chattarji; R. J. Kelleher, III; E.R. Kandel; K. Duff; A. Kirkwood; and J. Shen; "Loss of Presenilin Function Causes Impairments of Memory and Synaptic Plasticity Followed by Age-Dependent Neurodegeneration" Neuron, Apr. 8, 2004; vol. 42, pp. 23-36.

Dewji, Nazneen N.; D. Valdez; and S. J .Singer; "The presenilins turned inside out: Implications for their structures and functions" PNAS, Jan. 27, 2004, vol. 101, No. 4, pp. 1057-1062.

Pradier, Laurent; N. Carpentier; L. Delalonde; N. Clavel; M-D Bock; L. Buee; L. Mercken; B. Tocque; and C. Czech; "Mapping the APP/Presenilin (PS) Binding Domains: The Hydrophilic N-Terminus of PS2 Is Sufficient forInteraction with APP and Can Displace APP/PS1 Interaction" Neurobiology of Disease, 1999, vol. 6, pp. 43-55.

Smine, Abdelkrim; X. Xu; K. Nishiyama; T. Katada; P. Gambetti; S. P. Yadav; X.Wu; Y-C Shi; S. Yasuhara; V. Homberger; and T. Okamoto "Regulation of Brain G-protein G.sub.o , by Alzheimer's Disease Gene Presenilin-1" The Journal of Biological Chemistry; vol. 273, No. 26, pp. 16281-16288, Jun. 26, 1998.

(Continued)

*Primary Examiner* — John Ulm
(74) *Attorney, Agent, or Firm* — Joseph R. Baker, Jr.; Gavrilovich, Dodd & Lindsey LLP

(57) ABSTRACT

The disclosure relates generally to neurodegenerative disorders and more specifically to a group of presenilin/G-protein/c-src binding polypeptides and methods of use for modulating signaling and progression of Alzheimer's disease.

6 Claims, 10 Drawing Sheets

OTHER PUBLICATIONS

Dewji, Nazneen N.; C. Do; and S. J. Singer "On the spurious endoproteolytic processing of the presenilin proteins in cultured cells and tissues" Proc. Natl. Acad. Sci. U.S.A., Dec. 1997, vol. 94, pp. 14031-14036.

Dewji, Nazneen N., and S. J. Singer, "The seven-transmembrane spanning topography of the Alzheimer disease-related presenilin proteins in the plasma membranes of cultured cells" Proc. Natl. Acad. Sci. U.S.A. Dec. 1997, vol. 94, pp. 14025-14030.

Dewji, Nazneen N., and S. J. Singer, "Cell surface expression of the Alzheimer disease-related presenilin proteins" Proc. Natl. Acad. Sci. U.S.A., Sep. 1997, vol. 94, pp. 9926-9931.

Dewji, Nazneen N. and S. J. Singer; "Genetic Clues to Alzheimer's Disease" Science, Jan. 12, 1996, vol. 271, pp. 159-160.

Dewji, Nazneen N., and S. J. Singer "Specific transcellular binding between membrane proteins crucial to Alzheimer disease" Proc. Natl. Acad. Sci., U.S.A. Oct. 1996 vol. 93, pp. 12575-12580.

Ghidoni, R. et al., "Inhibition of energy metabolism down-regulates the Alzheimer related presenilin 2 gene," J. Nerual. Transm., 110(9):1029-1039 (2003).

Kitano et al., Production of polyclonal antibody specific for human natriuretic peptide receptor B, Journal of Immunological Methods 194(2):147-153 (1996).

Mercken et al., "Characterization of human presenilin-1 using N-terminal specific monoclonal antibodies: Evidence that Alzheimer mutations affect proteolytic processing," FEBS Letters 389(3):297-303 (1996).

Moyse, Ellen. International Preliminary Report on Patentability. Application No. PCT/US2007/007908. Date of Issuance of the report: Sep. 30, 2008.

Park, Yeong-Gwan. International Search Report and Written Opinion. Application No. PCT/US2010/034610. Date of Mailing: Feb. 9, 2011.

Shimojo, M. et al., "Enzymatic characteristics of I213T mutant presenilin-1/gamma-secretase in cell models and knock-in mouse brains: familial Alzheimer disease-linked mutation impairs gamma-site cleavage of amyloid precursor protein C-terminal fragment beta," J. Biol. Chem. 283(24):16488-16496 (2008).

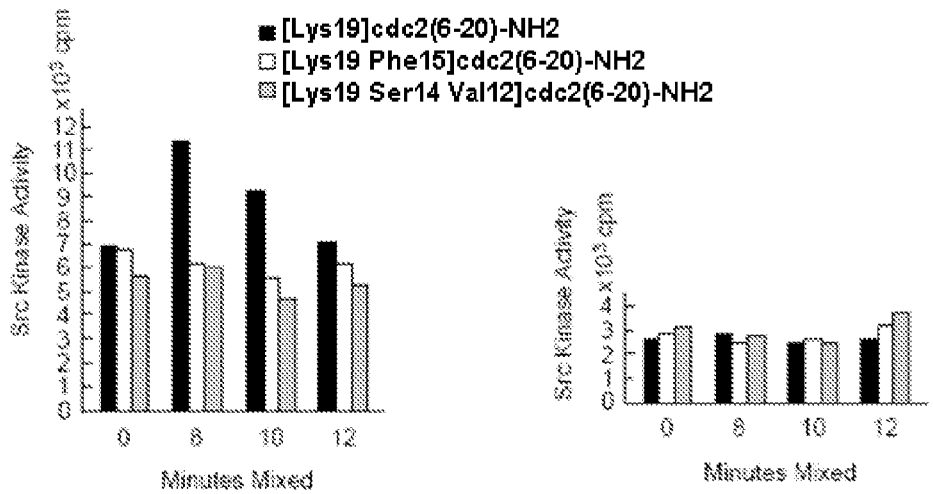
FIGURE 7A
FIGURE 7B
Extracts of B-APP-transfected DAMI with PS-2-transfected DAMI Cell Mixtures
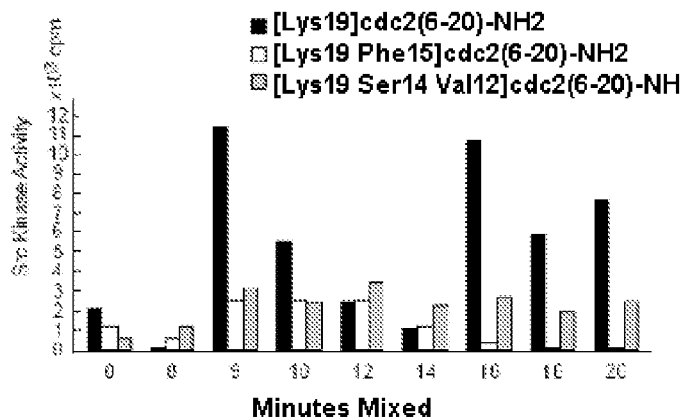
FIGURE 7C
Extracts of pcDNA3-transfected DAMI with PS-2-transfected DAMI Cell Mixtures
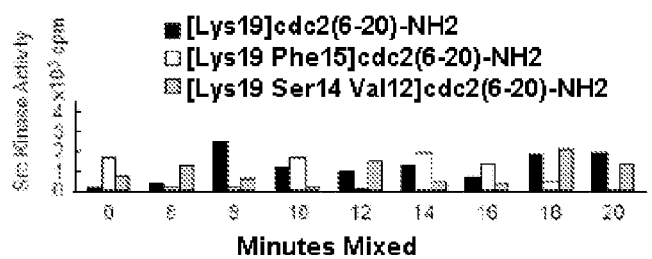
FIGURE 7D

Extracts of ß-APP-transfected DAMI with PS-1-transfected DAMI Cell Mixtures

Figurue 8B

Western blot hybridization

ß-APP-transfected DAMI + PS-1-transfected DAMI Mixed Cell Extracts

ß-APP-transfected ES-NULL + PS-1-transfected DAMI Mixed Cell Extracts

In-vitro phosphorylation following Anti-Src treatment
ß-APP-transfected DAMI + PS-1-transfected DAMI Mixed Cell Extracts β-APP-transfected DAMI + PS-2-transfected DAMI Mixed Cell Extracts Western blot hybridization Western blot hybridization In-vitro phosphorylation following Anti-Lyn treatment In-vitro phosphorylation following Anti-Fyn treatment

METHODS AND COMPOSITIONS FOR TREATING NEURODEGENERATIVE DISORDERS AND ALZHEIMER'S DISEASE AND IMPROVING NORMAL MEMORY

CROSS REFERENCE TO RELATED APPLICATIONS

This application is a continuation of U.S. patent application Ser. No. 11/693,926 filed Mar. 30, 2007 (now U.S. Pat. No. 7,851,228), which application claims priority to U.S. Provisional Application Ser. No. 60/788,524 filed Mar. 31, 2006, the disclosures of which are incorporated herein by reference.

STATEMENT REGARDING FEDERAL SPONSORED RESEARCH

This invention was made with government support under Grant No. AG07888, NS027580, and NS044768 awarded by the National Institutes of Health The government has certain rights in this invention.

FIELD OF THE INVENTION

The invention relates generally to treating neurodegenerative disorders and more specifically to a group of presenilin/G-protein/c-src binding polypeptides and small molecule drugs designed to modulate the physiologic interactions of polypeptides required for the production of β-amyloid (Aβ).

BACKGROUND

The presenilin (PS) proteins are ubiquitous polytopic integral membrane proteins that among other functions, are involved in the development of neurodegenerative disorders such as Alzheimer's disease (AD) and Down's syndrome (DS). AD is a degenerative disorder of the human central nervous system characterized by progressive memory impairment and cognitive and intellectual decline during mid to late adult life. The disease is accompanied by a variety of neuropathologic features principal among which are the presence in the brain of amyloid plaques and the neurofibrillary degeneration of neurons. The etiology of this disease is complex, although in about 10% of AD cases it appears to be familial, being inherited as an autosomal dominant trait. Among these inherited forms of AD, there are at least four different genes, some of whose mutants confer inherited susceptibility to this disease. The σ4 (Cys112Arg) allelic polymorphism of the Apolipoprotein E (ApoE) gene has been associated with AD in a significant proportion of cases with onset late in life. A very small proportion of familial cases with onset before age 65 years have been associated with mutations in the β-amyloid precursor protein (APP) gene on chromosome 21. A third locus associated with a larger proportion of cases with early onset AD has recently been mapped to chromosome 14q24.3. The majority (70-80%) of heritable, early-onset AD maps to chromosome 14 and appears to result from one of more than 20 different amino-acid substitutions within the protein presenilin-1 (PS1). A similar, although less common, AD-risk locus on chromosome 1 encodes a protein, presenilin-2 (PS-2, highly homologous to PS-1). Based upon mRNA detection, the presenilins appear to be ubiquitously expressed proteins, suggesting that they are normally housekeeping proteins required by many cell types.

Presenilin 1 is a 43-45 kDa polypeptide and presenilin 2 is a 53-55 kDa polypeptide. Presenilins are integral proteins of membranes present in high molecular weight complexes that are detergent sensitive. Three protein components of the complexes in addition to presenilin are known.

The functions of these interacting proteins could influence the specific intercellular binding of β-APP with PS, but so far no familial Alzheimer's disease (FAD) cases have been found where any of these three proteins are mutated. Missense mutations of presenilin 1 appear to destabilize and cause defective intracellular trafficking of β-catenin. Thus, differential interactions between presenilin polypeptides and proteins capable of specifically binding to presenilins may control particular roles of the normal and mutant forms of the presenilin polypeptides during development.

SUMMARY OF THE INVENTION

This invention provides methods and compositions for identifying agents that modulate activity of presenilins. Accordingly, the methods and compositions provided herein may be used to modulate the production of Aβ in the brain by (1): interfering with the binding of the extra-cellular N-terminal domain of β-APP with PS-1 or PS-2; or (2) by using as an inhibiting agent a small peptidomimetic molecule, or a small fragment of an antibody molecule directed to an epitope on either the interacting surfaces of the β-APP or PS molecules. In one aspect, the peptide is a soluble N-terminal domain of PS-1 or -2.

In one embodiment, a method of identifying an agent that modulates presenilin G-protein coupled receptor (GPCR) activity is provided. The method includes a) contacting presenilin, or fragment thereof, with a G-protein under conditions that would permit binding of the G-protein to presenilin; b) prior to, simultaneously with, or subsequent to a), contacting presenilin, or fragment thereof, with an agent; c) monitoring presenilin-mediated binding to the G-protein; and d) determining whether the agent modulates presenilin binding to the G-protein thereby identifying an agent that modulates presenilin G-protein coupled receptor (GPCR) activity. In some aspects the modulating is by inhibition of presenilin binding to the G-protein. In other aspects, the modulating is by activating presenilin binding to the G-protein. The presenilin can be presenilin-1 (PS-1) or presenilin-2 (PS-2). The G-protein can be $G_o$, $G_s$, $G_i$, $G_z$ or $G_q$.

In some aspects, the agent includes a naturally occurring or synthetic polypeptide or oligopeptide, a peptidomimetic, a small organic molecule, a polysaccharide, a lipid, a fatty acid, a polynucleotide, an RNAi or siRNA, an asRNA, or an oligonucleotide.

The methods provided herein may be conducted in vitro or in vivo. In some aspects, a method further includes contacting the presenilin with β-APP prior to, simultaneously with, or subsequent to contacting the presenilin with the G-protein.

In another embodiment, a method of identifying an agent that modulates presenilin-mediated Src protein kinase activity is provided. The method includes a) contacting presenilin, or fragment thereof, with β-APP under conditions that would permit binding of β-APP to presenilin; b) prior to, simultaneously with, or subsequent to a), contacting presenilin, or fragment thereof, with an agent; c) monitoring presenilin-mediated Src protein kinase activity; and d) determining whether the agent modulates presenilin-mediated Src protein kinase activity.

Also provided herein are compositions and methods for treating neurodegenerative disorders, and more specifically to a group of presenilin/G-protein/c-src binding polypeptides and small molecule drugs designed to modulate the physiologic interactions of polypeptides required for the production of β-amyloid (Aβ), the oligopeptide that is the primary neurotoxic agent in Alzheimer's disease (AD). The objective is to reduce the amount of Aβ in the brain to an extent that significantly decreases the neurotoxicity in AD, or delays the onset, or decreases the severity of the disease. and methods of use for modulating signaling and progression of Alzheimer's Disease and improve memory The invention also provides a method of inhibiting the production of Aβ with a small molecule agent that inhibits the interaction of PS-1 or PS-2 with the G-proteins $G_{oA}$ and $G_{oB}$. The cytoplasmic C-terminal and other domains of PS-1 or PS-2 have been shown by us to be the sites of interaction of $G_{oA}$ and/or GoB with PS, and that this $G_o$-PS intracellular binding is required for subsequent Aβ production, presumably via the downstream results of this binding process.

The invention similarly provides a method of inhibiting the production of Aβ by contacting a cell expressing a PS-1 and/or PS-2 with an agent that interferes with the downstream results of PS-1 and/or PS-2 binding to $G_o$ such as $G_o$ activation with phospholipase C.

The invention also provides a method of inhibiting the production of Aβ by the use of small molecules, peptides or antibodies selected to interfere with the activities of members of the Src family of tyrosine kinases.

The invention further provides a method of assaying for inhibitors of Aβ production in a cell culture system consisting of a first transfected cell type expressing β-APP but no PS mixed with a second cell type expressing PS but no β-APP. The inhibitory effect of an agent added to this mixed cell culture would be measured from the activities of several likely downstream effects of (a) the $G_{oA}$ and $G_{oB}$ interaction with PS-1 and PS-2; or (b) the Src family of tyrosine kinases; or (c) the interaction of N-terminal domain of βAPP with the N-terminal domain of PS-1 and/or PS-2.

In another aspect, the invention provides a method of improving cognitive function and/or memory in a subject. The method includes administering an agent that inhibits the interaction of PS-1 and/or PS-2 with G-protein, $G_{oA}$ and $G_{oB}$. In one approach, the agent interacts with the C-terminal tail and/or other cytoplasmic domains of PS-1 and/or 2 that interact with $G_{oA}$ and/or $G_{oB}$. The agent may also interfere with the downstream results of PS-1 and/or PS-2 binding to $G_o$ such as $G_o$ activation with phospholipase C. In another approach, the agent inhibits the activity of members of the Src family of tyrosine kinases in cells expressing PS-1 and/or PS-2. In each case the agent would be administered in an amount to improve cognitive function and/or memory retention compared to a control subject.

DESCRIPTION OF DRAWINGS

FIG. 7A-D show Experiments to determine the nature of the tyrosine phosphorylating enzyme activity in FIG. 6. Src family kinase assay with synthetic peptides. a and b: β-APP:PS-1 interaction with separately transfected DAMI cells as a function of time after mixing. Src kinase activity was assayed using the Src family substrate peptide {lys19}cdc2(6-20)-NH2 (black bars) and control peptides {lys19Phe15}cdc2(6-20)NH2 (white bars) and {lys19ser14val12}cdc2(6-20)NH2 (gray bars) for both the β-APP:PS-1 (a) and control pcDNA3:PS-1 (b) interactions. c and d: β-APP:PS-2 interaction with separately transfected DAMI cells as a function of time after mixing. Src kinase activity was assayed using the Src family substrate peptide {lys19}cdc2(6-20)-NH2 (black bars) and control peptides {lys19Phe15}cdc2(6-20)NH2 (white bars) and {lys19ser14val12}cdc2(6-20)NH2 (gray bars) for both the β-APP:PS-2 (c) and control pcDNA3:PS-2 (d) interactions.

FIG. 8A-B shows inhibition of tyrosine kinase activity. ELISAs to demonstrate tyrosine kinase activity of DAMI cells which had been separately transfected with β-APP and PS-1 and mixed in the presence and absence of 10 μg/ml Herbimycin A (a) and 10 nM PP2 (b), as a function of time after mixing.

DETAILED DESCRIPTION

Figure 1:
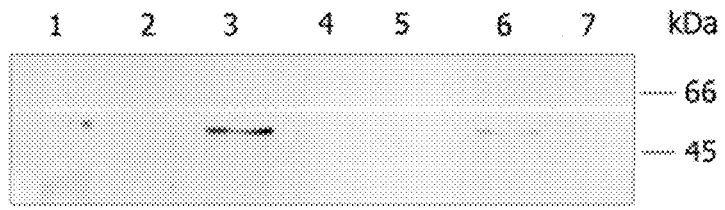
FIG. 1 shows a representative study to determine if PS-1 is a GPCR. Extracts of different cell cultures were analyzed in order to determine whether $G_o$ interacts with PS-1, including the necessary controls. In each lane, the particular cell extracts were first immunoprecipitated with a monoclonal Ab (MAb) directed to PS-1; the immunoprecipitate was then dissolved and subjected to SDS-PAGE electrophoresis, and the resulting gel was Western blotted with an antibody directed to $G_o$ (this antibody recognizes both $G_{oA}$ and $G_{oB}$) Lane 1 is a control of an extract of untransfected ES (PS-1$^{-/-}$/PS-2$^{-/-}$)cells. As expected, this extract showed that no $G_{oA}$ (or $G_{oB}$) was immunoprecipitated with Ab to PS-1. Lane 2 is an extract of ES cells, that had first been transfected with PS-1 only, but not with $G_{oA}$. No protein band was observed for $G_{oA}$; this was another control experiment. Lane 3 is an extract of the ES cells transfected with both PS-1 and $G_{oA}$. In this extract, $G_{oA}$ is immunoprecipitated along with the PS-1, showing that PS-1 was bound to $G_{oA}$, but not $G_{oB}$. If PS-1 without its C-terminal "tail" (lane 4), which protrudes from the membrane into the aqueous intracellular compartment), is transfected into ES double null cells along with $G_{oA}$ (lane 6), little or no $G_{oA}$ is immunoprecipitated along with the PS-1 tailless, showing that the C-terminal domain of PS-1 is the principal region of $G_{oA}$ binding to PS-1.

As used herein, the singular forms "a," "and," and "the" include plural referents unless the context clearly dictates otherwise. Thus, for example, reference to "a protein" includes a plurality of such proteins and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The invention is based, in part, upon the interaction of various G-protein coupled receptors (GPCRs), as well as their downstream effectors, protein kinase activity and calcium homeostasis. GPCRs comprise one of the largest gene families in the human genome, and mediate a huge variety of cellular functions regulated by neurotransmitters, hormones, chemokines, and many other molecules. Timely uncoupling of GPCR signaling is crucial for maintaining appropriateness and integrity of the GPCR-mediated physiological functions. This uncoupling is primarily mediated by a much smaller gene family, currently numbering seven members of GPCR kinases (GRKs). The specificity for a few GRK members to regulate a huge numbers of GPCRs is controlled in an agonist-dependent manner. In another words, GRKs preferentially bind to and phosphorylate agonist-occupied GPCRs to uncouple receptor from corresponding G-protein, a process known as homologous desensitization. Based on structural similarities, seven known GRK members are classified into four subfamilies (GRK1, GRK2/3, GRK4/5/6 and GRK7), with GRK2/3 and GRK5/6 having ubiquitous distributions including brain. Dysregulation of GRK2, probably GRK5 as well, has been implicated in the pathogenesis of chronic heart failure, myocardial ischemia, and hypertension, and other cardiovascular disorders, where the GRKs have been extensively studied. Failure to desensitize rhodopsin signaling by GRK1 can lead to photoreceptor cell death, and is believed to contribute to retinitis pigmentosa. In addition, increased GRK2 levels have been associated with opiate addiction. Aside from these, however, roles of GRKs in many other pathological conditions potentially associated with GPCR deregulation, such as in AD, remain virtually unexplored.

Due to the membrane location of GPCRs, GRK's retention on the plasma membrane or in the cytosol physically affects its access and binding to GPCRs. In resting cells, GRK4 subfamily members (including GRK4/5/6) are tightly associated with the plasma membrane (Reference 10), while GRK2 subfamily members (GRK2/3) are primarily cytosolic and translocate to the membrane when cells are stimulated by GPCR agonists. However, in active cells, subcellular localization of GRKs appears to be determined by the content and capacity of GRK-binding factors in membrane versus cytosol. Phospholipids, particularly phosphatidylinositol-4,5-biphosphate, appear to play a role in GRKs adherence to the membrane and bind GPCRs, while phosphatidylserine (PS) may also enhance GRK2 binding to GPCRs on the membrane. On the other hand, calcium/calmodulin and other calcium-binding proteins, as well as actin, actinin, and the like may contribute to sequester GRKs in the cytosol and inhibit binding of GRKs to GPCRs.

In AD brains, significant membrane alterations, aberrant phosphoinositide metabolism, disrupted calcium homeostasis and disorganized cytoskeleton proteins could all influence the subcellular distribution of GRKs. In addition, increased β-amyloid, a hydrophobic peptide central to AD pathogenesis, has been shown to decrease membrane phosphatidylinositol-4,5-biphosphate and increase $[Ca^{2+}]_i$.

Evidence of a 7-TM structure (like that of rhodopsin) for PS-1 and PS-2 has led to the examination regarding whether PS-1 and PS-2 belong to the G-Protein coupled receptor superfamily of proteins, which all share essentially a similar structure. Although PS does not exhibit any substantial amino acid homologies with any of the approximately 1,000 GPCR's so far examined, the fact that all of these GPCR's are 7-TM integral proteins, with many showing no sequence homologies with any others, allows for the possibility that PS molecules are also GPCR's. GPCR activity of PS was identified using a N141I-PS-2 mutation. The mutation, linked with FAD in Volga German families, caused PC-12 cell death in a Pertussis toxin (PTx) sensitive manner. Other studies suggested that within the 39 amino acid residue carboxyl-terminal domain of PS-1 (located in the cytoplasm in almost all topographic models of PS-1 in the membrane) there exists a specific binding and regulating domain for the brain $G_o$ protein. This domain of PS-1 that binds $G_o$ in vitro also shows some local amino acid sequence homologies with the G-binding domains of two other GPCR proteins, the D2-dopaminergic, and the 5HT-1B receptors, as well as the G-protein activating oligopeptide, mastoparan. The possibility that PS-1 may be a functional GPCR is further described herein.

The present disclosure demonstrates that G-protein $G_o$ binds full-length PS-1, and is inhibited by Pertussis toxin. In addition, only $G_{oA}$ binds PS-1, not $G_{oB}$. Transfection of ES null cells with a tail-less construct of PS-1, demonstrates that most of the binding occurs at the carboxyl terminal tail of PS-1. However, these results also indicate that other cytoplasmic loop regions may be involved in the binding, since very small amounts of binding occurred in the presence of tail-less PS-1. The disclosure also demonstrates that the G-protein binds not only to PS-1 but also PS-2 and that for PS-2, in addition to the binding of $G_{oA}$, $G_{oB}$ also binds intact PS-2, not seen for PS-1. This binding is still present when tail-less PS-2 is used in place of full-length PS-2. These results suggest that $G_{oB}$ binds PS-2 at a cytoplasmic domain other than the C-tail. A greater than 700% increase in $^{35}$S-GTPγS-labeled $G\alpha_{oA}$ (but not $G\alpha_{oB}$) binding to PS-1. For PS-2 there is similarly a greater than 700% increase over basal levels of $^{35}$S-GTPγS-labeled $G\alpha_{oA}$ binding as well as ~300% increase in $^{35}$S-GTPγS-labeled $G\alpha_{oB}$. Treatment with PTx inhibits the incorporation of 35S-GTPγS to both $G_{oA}$ and $G_{oB}$.

Thus, $G_{oA}$ appears to bind both PS-1 and PS-2 at similar rates, whereas the binding of $G_{oB}$ to PS-2 is less than half that observed for $G_{oA}$ under the same experimental conditions. The data confirm a functional consequence of the G-protein coupling to PS-1 and PS-2 and further characterize the two presenilin proteins as G-protein coupled receptors (GPCRs).

GPCRs have been classified into three main families according to their sequence homology and structural features. Family 1 is the largest, constituting 90% of all GPCRs. Members of this family have a short amino terminal extracellular domain and several conserved amino acid motifs within the 7-TM domain. A "signature" of family 1 GPCRs is a conserved tripeptide DRY sequence at the interface of TM-III and 2nd intracellular loop that plays a critical role in G-protein coupling. PS-1 and PS-2 have none of the conserved family 1 motifs, including the DRY sequence, and are unlikely to belong to this group. Members of family 2 share a longer extra-cellular domain and are activated by large peptide ligands such as glucagons and secretin. Members of family 3 include the metabotropic glutamate receptors (mGluRs), γ-aminobutyric acid B ($GABA_B$) receptors and the extra-cellular cation-sensing $Ca^{2+}$ receptor and have large extra-cellular domains that function as ligand-binding domains. It is thought that this family utilizes distinct intracellular domains and mechanisms for G-protein signaling. The conserved amino acid motifs and DRY sequence present in family 1 GPCRs are not conserved in family 3 and it is thought that the molecular events that lead to a conformational change in the proteins are therefore somewhat distinct between members of family 1 and family 3 GPCRs.

PS-1 and PS-2 appear to have more features in common with family 3 GPCRs than with either of the other two families—both have large extra-cellular domains (the N-terminal, and the hydrophilic loop between TM VI and VII), a feature of family 3 GPCRs. Ligand binding in family 3 GPCRs appears to take place exclusively via the extra-cellular domains, generally the amino terminal domain. The N-terminal domain of PS-1 or PS-2 is sufficient for in vitro binding of PS-1 or PS-2 respectively, to β-APP, a proposed ligand and possible agonist of PS GPCR activation. Some family 3 members form homodimers, usually by di-sulfide bonds via extra-cellular Cys residues. It is well known that PS-1 and PS-2 exist in the membrane as dimers. Further, they both have Cys residues in their extra-cellular domains (7-TM structure), although it is not known whether these form di-sulfide bonds and participate in dimerization of the proteins. Family 3 GPCRs all have the 3rd intracellular loop as the shortest loop and this is conserved among each type. Likewise, the third intracellular loop in PS-1 and PS-2 is the shortest loop, consisting of the sequence KYLPEW (SEQ ID NO:1), which is completely conserved. Some members of family 3 GPCRs interact directly via their carboxyl terminal PDZ binding domains with intracellular PDZ-domain proteins such as Homer. There is a PDZ binding domain in the carboxyl terminal tail of PS-1 which has been shown to bind to several PDZ proteins.

Studies on the mechanisms of Aβ production have involved cell-cell interaction of β-APP on the surface of one cell with PS-1 or PS-2 on the surface of another cell. The invention suggests that the β-amyloid precursor protein β-APP and PS-1 or 2 may normally be components of an intercellular signaling system. One or more forms of β-APP can specifically bind either to PS-1, or PS-2, via their extracellular domains that protrude from their respective cell membranes. This binding in vivo induces an intercellular signaling event of significance to normal neural physiology or development. A by-product of this transcellular molecular binding, processes of vesicle formation, cellular internalization, and proteolytic degradation are set in motion that result in the formation and cellular release of Aβ and its slow accumulation in regions of the brain.

PS are expressible at the cell-surface and have 7-TM structures and PS-1 and PS-2 participate in a specific cell-cell interaction with β-APP; this β-APP:PS mediated intercellular interaction results in transient increase in tyrosine kinase activity and protein tyrosine phosphorylation. Furthermore, a β-APP:PS mediated cell-cell interaction is required for at least the major part of the production of Aβ. The intercellular interaction between β-APP and PS may also activate G-protein binding to PS. (There is now substantial evidence that there is cross-talk between protein tyrosine kinases and the G-protein signaling pathways).

If $G_o$ activation by PS ultimately affects Aβ production, then a possible outcome of these last studies might be a drug therapy for AD using appropriately designed inhibitors of PS-$G_o$ specific binding.

Thus, it appears that PS-1, PS-2 and APP play a role in intracellular signaling. The primary focus of investigations of these three proteins has been on their respective roles in the proteolytic fragmentation of β-APP to Aβ that involves the PS proteins either directly or indirectly. In addition, one or more forms of β-APP on one cell surface and PS-1 (or PS-2) on another may be specific ligand and receptor components of an intercellular signaling system with a role in normal physiology. The disclosure provides evidence that intercellular surface binding of β-APP to the PS proteins functions in normal physiology to induce a signaling process within one, or possibly both, of the adherent cells, leading ultimately to a developmental outcome significant for the organism.

This proposal was based on an analogous intercellular signaling between pre-R7 and R8 cells in the development of the *Drosophila* eye. In *Drosophila*, the Type I single-TM spanning protein Sevenless (SEV) (similar to β-APP) on the pre-R7 cell surface binds specifically to the 7-TM Bride of Sevenless (BOSS) protein (similar to PS-1 or PS-2). As described elsewhere herein, the PS proteins are of 7-TM topography, not 8, as widely accepted. In this case, signaling requires that the tyrosine kinase activity of the cytoplasmic domain of the SEV protein be activated. Neither β-APP nor the PS proteins are protein tyrosine kinases and if protein tyrosine phosphorylation were involved, another indirect activity of the cytoplasmic domain(s) would, in this case, have to provide the downstream signal. Experiments were initially undertaken to detect such possible intercellular protein tyrosine phosphorylation signaling events. It was shown that when cultured DAMI (human megakaryoblast) cells that were transiently transfected with β-APP were mixed with DAMI cells transfected with PS-1, or PS-2, within several minutes after mixing, the cell extracts showed significant transient increases in protein tyrosine kinase activity and in phosphotyrosine (PTyr) modification of protein substrates, that did not appear in controls, or in cell mixtures containing inhibitors of the specific β-APP:PS binding. The downstream consequences of this signaling were different depending on whether PS-1 or PS-2 was engaged in the intercellular binding to β-APP, because the spectrum of proteins that showed enhanced tyrosine phosphorylation was altogether different in the two cases, suggesting a distinction between, rather than a redundancy of, the biochemical functions of the two closely homologous PS proteins.

The disclosure demonstrates the biological pathways by using embryonic stem (ES) cells derived from PS-1$^{-/-}$, PS-2$^{-/-}$ double null mice herein referred to as ES double-null cells, either untransfected in control experiments, or transfected with β-APP. In the latter case, the β-APP-transfected ES cells are mixed with either PS-1- or PS-2-transfected DAMI cells; the DAMI cells do not express significant amounts of endogenous β-APP on their surfaces. In this mixed cell-culture system, therefore, the β-APP-transfected ES double-null cells serve as the only source of cell-surface expressed β-APP, while the PS-transfected DAMI cells are the only source of cell-surface expressed PS. If a β-APP:PS specific signaling event occurs in this system, it can be the result of a juxtacrine interaction between the two cell types. In the present study, such an interaction has been found.

The increase in PTyr protein modification that is the consequence of β-APP:PS intercellular binding involves a protein tyrosine kinase(s) to be determined. Evidence is provided that signaling is accompanied by transient elevations in Src family tyrosine kinase activity, and has identified the individual Src family member mediating the intercellular signaling between β-APP and PS-1, but not PS-2, to be pp60c-src. In contrast, the β-APP:PS-2 signaling involves the Src family member Lyn. These signaling events affect normal physiology. For example, they may play a role in the physiological defects encountered in the development of β-APP null mice.

The Src family of kinases are implicated in cancer, immune system dysfunction and bone remodeling diseases. For general reviews, see Thomas and Brugge, Annu. Rev. Cell Dev. Biol. 1997, 13, 513; Lawrence and Niu, Pharmacol. Ther. 1998, 77, 81; Tatosyan and Mizenina, Biochemistry (Moscow) 2000, 65, 49-58; Boschelli et al., Drugs of the Future 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. Biochemistry (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This shows that osteoporosis resulting from abnormally high bone resorption is treated by inhibiting Src. Soriano et al., Cell 1992, 69, 551 and Soriano et al., Cell 1991, 64, 693.

Suppression of arthritic bone destruction has been achieved by the overexpression of CSK in rheumatoid synoviocytes and osteoclasts. Takayanagi et al., J. Clin. Invest. 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., Drugs of the Future 2000, 25(7), 717.

Src also plays a role in the replication of hepatitis B virus. The virally encoded transcription factor HBx activates Src in a step required for propagation of the virus. Klein et al., EMBO J. 1999, 18, 5019, and Klein et al., Mol. Cell. Biol. 1997, 17, 6427.

A number of studies have linked Src expression to cancers such as colon, breast, hepatic and pancreatic cancer, certain B-cell leukemias and lymphomas. Talamonti et al., J. Clin. Invest. 1993, 91, 53; Lutz et al., Biochem. Biophys. Res. 1998 243, 503; Rosen et al., J. Biol. Chem. 1986, 261, 13754; Bolen et al., Proc. Natl. Acad. Sci. USA 1987, 84, 2251; Masaki et al., Hepatology 1998, 27, 1257; Biscardi et al., Adv. Cancer Res. 1999, 76, 61; Lynch et al., Leukemia 1993, 7, 1416. Furthermore, antisense Src expressed in ovarian and colon tumor cells has been shown to inhibit tumor growth. Wiener et al., Clin. Cancer Res., 1999, 5, 2164; Staley et al., Cell Growth Diff. 1997, 8, 269.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., Nature, 1992, 357, 161. Hck, Fgr and Lyn have been identified as important mediators of integrin signaling in myeloid leukocytes. Lowell et al., J. Leukoc. Biol., 1999, 65, 313. Inhibition of these kinase mediators may therefore be useful for treating inflammation. Boschelli et al., Drugs of the Future 2000, 25(7), 717.

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., Curr. Biol., 4, 1077-86 (1994); and Brownlees et al., Neuroreport 8, 3251-55 (1997); Kaytor and Orr, Curr. Opin. Neurobiol., 12, 275-8 (2000)]. In transgenic mice overexpressing GSK3, significant increased Tau hyperphosphorylation and abnormal morphology of neurons were observed (Lucas et al., EMBO J, 20:27-39 (2001)). Active GSK3 accumulates in cytoplasm of pretangled neurons, which can lead to neurofibrillary tangles in brains of patients with AD (Pei et al., J Neuropathol Exp Neurol, 58, 1010-19 (1999)). Therefore, inhibition of GSK-3 slows or halts the generation of neurofibrillary tangles and thus treats or reduces the severity of Alzheimer's disease.

Evidence for the role GSK-3 plays in Alzheimer's disease has been shown in vitro. See Aplin et al. (1996), J Neurochem 67:699; Sun et al. (2002), Neurosci Lett 321:61 (GSK3b phosphorylates cytoplasmic domain of Amyloid Precursor Protein (APP) and GSK3b inhibition reduces Ab40 and Ab42 secretion in APP-transfected cells); Takashima et al. (1998), PNAS 95:9637; Kirschenbaum et al. (2001), J Biol Chem 276:7366 (GSK3b complexes with and phosphorylates presenilin-1, which is associated with gamma-secretase activity in the synthesis of Ab from APP); Takashima et al. (1998), Neurosci Res 31:317 (Activation of GSK3b by Ab(25-35) enhances phosphorylation of tau in hippocampal neurons. This observation provides a link between Ab and neurofibrillary tangles composed of hyperphosphorylated tau, another pathological hallmark of AD); Takashima et al. (1993), PNAS 90:7789 (Blockade of GSK3b expression or activity prevents Ab-induced neuro-degeneration of cortical and hippocampal primary cultures); Suhara et al. (2003), Neurobiol Aging. 24:437 (Intracellular Ab42 is toxic to endothelial cells by interfering with activation of Akt/GSK-3b signaling-dependent mechanism); De Ferrari et al. (2003) Mol Psychiatry 8:195 (Lithium protects N2A cells and primary hippocampal neurons from Ab fibrils-induced cytotoxicity, & reduced nuclear translocation/destabilization of (β-catenin); and Pigino et al., J Neurosci, 23:4499, 2003 (The mutations in Alzheimer's presenilin 1 may deregulate and increase GSK-3 activity, which in turn, impairs axonal transport in neurons. The consequent reductions in axonal transport in affected neurons can ultimately lead to neurodegeneration).

Evidence for the role GSK-3 plays in Alzheimer's disease has been shown in vivo. See Yamaguchi et al. (1996), Acta Neuropathol 92:232; Pei et al. (1999), J Neuropath Exp Neurol 58:1010 (GSK3b immunoreactivity is elevated in susceptible regions of AD brains); Hernandez et al. (2002), J Neurochem 83:1529 (Transgenic mice with conditional GSK3b overexpression exhibit cognitive deficits similar to those in transgenic APP mouse models of AD); De Ferrari et al. (2003) Mol Psychiatry 8:195 (Chronic lithium treatment rescued neurodegeneration and behavioral impairments (Morris water maze) caused by intrahippocampal injection of Ab fibrils.); McLaurin et al., Nature Med, 8:1263, 2002 (Immunization with Ab in a transgenic model of AD reduces both AD-like neuropathology and the spatial memory impairments); and Phiel et al. (2003) Nature 423:435 (GSK3 regulates amyloid-beta peptide production via direct inhibition of gamma secretase in AD tg mice).

Presenilin-1 and kinesin-1 are also substrates for GSK-3 and relate to another mechanism for the role GSK-3 plays in Alzheimer's disease, as was recently described by Pigino, G., et al., Journal of Neuroscience (23:4499, 2003). It was found that GSK3beta phosphorylates kinsesin-1 light chain, which results in a release of kinesin-1 from membrane-bound organelles, leading to a reduction in fast anterograde axonal transport. A mutations in PS-1 may deregulate and increase GSK-3 activity, which in turn, impairs axonal transport in neurons. The consequent reductions in axonal transport in affected neurons ultimately lead to neurodegeneration.

The invention supports that specific adhesion between β-APP-presenting and PS-presenting cells might have different physiological consequences, one a transcellular (juxtacrine) signaling process associated with the normal function of these proteins, and the other resulting eventually in the proteolysis of β-APP to form Aβ, leading to the pathology of Alzheimer's disease. Evidence for a juxtacrine interaction in this system was obtained with cultured DAMI cells appropriately transfected with either β-APP, or with PS-1 or PS-2; a specific β-APP:PS mediated cell-cell interaction led to rapid and transient increases in protein tyrosine kinase activity and protein tyrosine phosphorylation within most likely one, or possibly both, of the adhering cells. DAMI cells were employed because these cells do not normally express significant amounts of endogenous β-APP at the cell surface, and because they are easy to detach mechanically from the cell substratum. Thus, by transfecting ES double-null cells with β-APP, cells expressing only surface β-APP but not PS were made available, and by transfecting DAMI cells with either PS-1 or PS-2, additional cells were produced that expressed a PS protein at the surface, and no significant β-APP.

Figure 5:
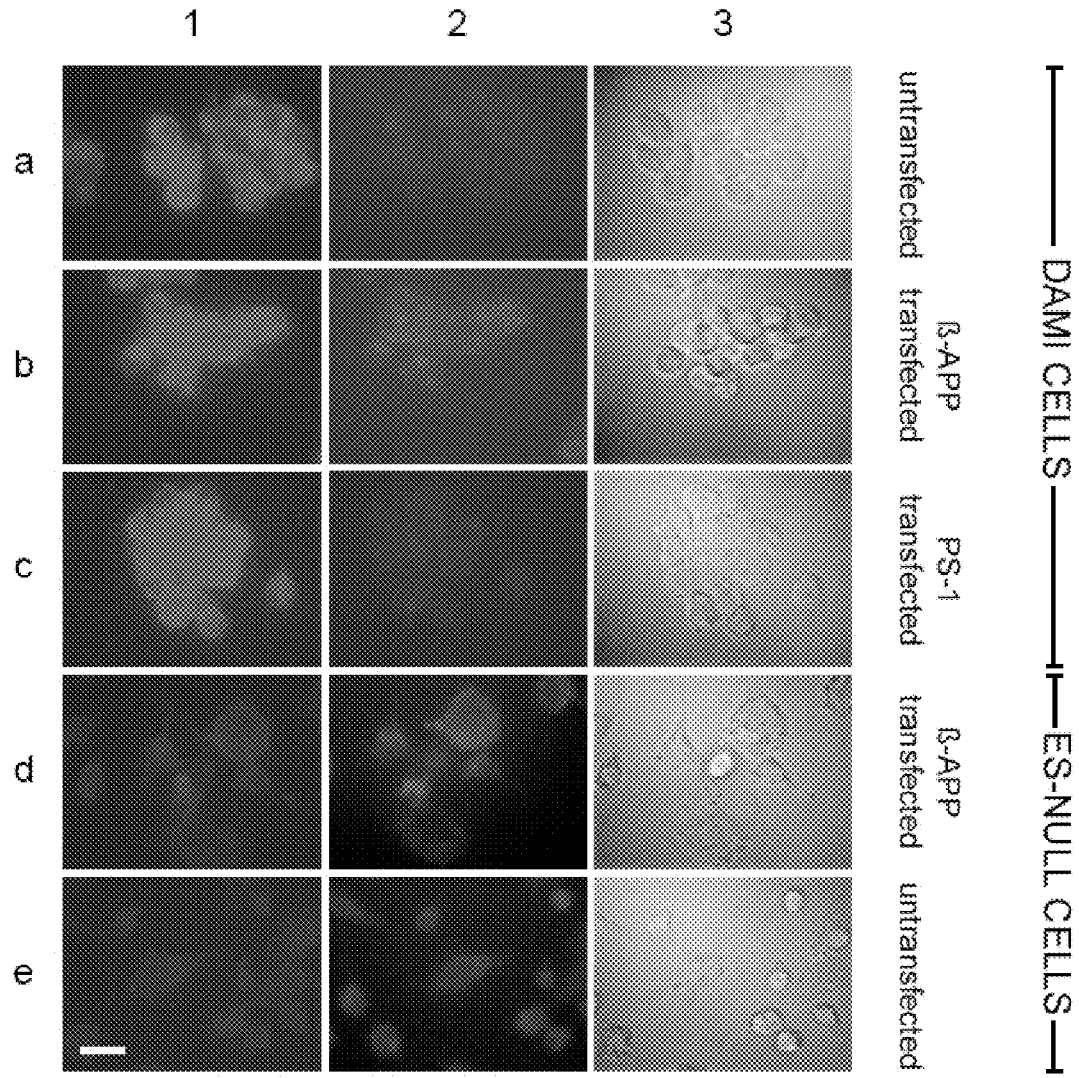
FIG. 5 A-E shows immunofluorescence microscopic labeling of fixed cells. a) Double immunofluorescence microscopic labeling of untransfected, fixed but not permeabilized, DAMI cells with primary rat Mab #1563 to human PS-1 N-terminal domain (Panel 1) and FITC conjugated anti-rat IgG secondary antibody shows cell-surface immunolabeling of endogenous PS-1 amino terminal domain. Panel 2 shows the same cells do not express appreciable amounts of cell-surface β-APP when labeled with Mab #348 to the β-APP extracellular domain and TRITC-conjugated anti-mouse IgG secondary antibody. Panel 3 shows the Nomarski images of cells in panels 1 and 2. b) Double Immunofluorescence microscopic labeling of β-APP-transfected, fixed but not permeabilized, DAMI cells shows cell-surface expressed β-APP when labeled with Mab #348 to the β-APP extracellular domain and TRITC-conjugated secondary antibody (Panel 2). Panels 1 and 3, the same cells treated as for FIG. 5a. c) Immunofluorescence microscopic labeling of PS-1-transfected, fixed but not permeabilized, DAMI cells shows high expression of cell-surface PS-1 (Panel 1) but not β-APP (Panel 2) when labeled with the same primary and secondary antibodies described in a. Panel 3 shows the Nomarski image of cells in panels 1 and 2. These experiments show that transfection of the DAMI cells with PS-1 does not call forth cell surface expression of β-APP. d) Immunofluorescence microscopic labeling of β-APP-transfected, fixed but not permeabilized ES cells, double-null for PS-1 and PS-2. Cells show cell-surface expressed β-APP when labeled with Mab #348 to the β-APP extracellular domain and TRITC-conjugated secondary antibody (Panel 2). Panel 1 shows the result of labeling with primary rat Mab #1563 to human PS-1 N-terminal domain and FITC conjugated appropriate secondary antibody, indicating the expected absence of PS-1 on the surfaces of ES double-null cells. Panel 3 shows Nomarski image of cells in Panels 1 and 2. e) Immunofluorescence microscopic labeling of untransfected, fixed but not permeabilized ES cells, double-null for PS-1 and PS-2. Cells show cell-surface expressed endogenous mouse β-APP when labeled with Mab #348 to the β-APP extracellular domain and TRITC-conjugated secondary antibody (Panel 2). Panels 1 and 3 labeled as in d; no cell surface labeling for PS-1 (Panel 1) is observed in these untransfected ES cells. Bar, 20 μm.

Mixing experiments between these transfected cells, as the results show, clearly reveal signaling specifically between β-APP and PS (FIG. 5), which result from a juxtacrine interaction; i.e., a reaction involving membrane-bound PS on one cell surface with β-APP on another. This interaction is specifically inhibited both by soluble β-APP (the exoplasmic domain of β-APP), and by the N-terminal domain of PS-1 fused to FLAG, demonstrating the dual specificity of the interaction of β-APP with PS.

The downstream consequences of this signaling are different depending on whether PS-1 or PS-2 is engaged in the intercellular binding to β-APP. The spectrum of proteins modified by tyrosine phosphorylation differed depending on whether PS-1 or PS-2 was involved in the specific intercellular binding to β-APP. Here the invention identifies c-Src as a protein that undergoes the major transient increases in phosphorylation when β-APP and PS-1 interact intercellularly, yet it appears not to be involved in the increase in Src family kinase activity observed when β-APP undergoes cell-cell interaction with PS-2. For the latter, the Src kinase family member Lyn appears to be the predominant (or at least a major) Src kinase involved. Together these results suggest distinct signaling mechanisms that might result in different rather than redundant physiological functions for the two closely homologous presenilin proteins.

The invention demonstrates that juxtacrine signaling between β-APP and either PS-1 or PS-2 results in rapid transient tyrosine kinase activation that are differentiable between the two PS proteins. However, none of these proteins are themselves tyrosine kinases, and some types of indirect activation of Src family kinase activities seem to be involved. In general, members of the Src family of tyrosine kinases can be activated indirectly by binding to receptors or other proteins using a variety of different molecular mechanisms. Src tyrosine kinases can be regulated by binding to specific receptors and they in turn can regulate the functional activity of the receptors. C-Src or Lyn may be recruited upon the binding of β-APP with PS-1 or PS-2, respectively. Recruitment would suggest that a signaling complex is formed transiently in vivo at sites of cell-cell contact, setting in motion a cascade of phosphorylation events that could result in developmental consequences. Identifying the region(s) of Src necessary for association with the β-APP:PS-1 complex should yield valuable information regarding the assembly and activation of a β-APP:PS-1 signaling complex and should indicate whether or not the interaction between the β-APP:PS complex and the kinases is direct or indirect. β-APP is not known to be phosphorylated on cytoplasmic tyrosine residues, and neither is PS-1, so direct binding through the SH2 domain of c-Src is unlikely since this domain binds only at phosphorylated tyrosine residues.

Direct binding may however alternatively occur via the SH3 domain of Src. SH3 domains recognize proline-rich sequences containing the core P-X-X-P (SEQ ID NO:2), where X denotes any amino acid. Ligands recognize the SH3 binding surface in one of two opposite orientations. Peptides that bind in a type 1 orientation conform to the consensus sequence R-X-L-P-X-Z-P (SEQ ID NO:3) where Z is normally a hydrophobic or Arg residue (Kay et al., 2000). Interestingly, both PS-1 and PS-2 have a conserved type 1 SH3 binding site (LPALP) in the cytoplasmic carboxyl terminal region (residues 432-436 of PS-1 and residues 412-416 of PS-2), but the identity of these SH3 binding sites does not account for the differentiable activation of PS-1 and PS-2 by β-APP.

Tyrosine phosphorylation has been implicated in the regulation of a variety of biological responses and the tyrosine kinases involved in mediating these responses are made up of a diverse spectrum of proteins. Src kinases have been implicated in adhesion events regulated by the receptors they bind and are activated following engagement of multiple receptor pathways that regulate cell-cell and cell-matrix interactions. It seems likely that β-APP:PS signaling might play a significant role in normal developmental physiology. Whether such signaling is in addition a required early step in the pathway of Aβ production, might be experimentally investigated by determining the effect of inhibiting the juxtacrine tyrosine phosphorylation on Aβ production.

A number of agents that inhibit GPCR interactions are known in the art. In addition, a number of kinase (e.g., c-src, fln and the like) inhibitors are known in the art and can be used in the methods of the invention. Compositions comprising such agents in pharmaceutically acceptable carriers for treating AD are contemplated by the invention.

GPCRs share a common structural motif. Generally, these receptors have seven sequences of between 22 to 24 hydrophobic amino acids that form seven alpha helices, each of which spans the membrane (each span is identified by number, i.e., transmembrane-1 (TM-1), transmebrane-2 (TM-2), etc.). The transmembrane helices are joined by strands of amino acids between transmembrane-2 and transmembrane-3, transmembrane-4 and transmembrane-5, transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins exist, currently, Gq, Gs, Gi, Gz and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Receptor activated G proteins are bound to the inside surface of the cell membrane. They consist of the Gα and the tightly associated Gβγ subunits. When a ligand activates the G protein-coupled receptor, it induces a conformation change in the receptor (a change in shape) that allows the G protein to now bind to the receptor. The G protein then releases its bound GDP from the Gα subunit, and binds a new molecule of GTP. This exchange triggers the dissociation of the Gα subunit, the Gβγ dimer, and the receptor. Both, Gα-GTP and Gβγ, can then activate different signalling cascades (or second messenger pathways) and effector proteins, while the receptor is able to activate the next G protein. The Gα subunit will eventually hydrolyze the attached GTP to GDP by its inherent enzymatic activity, allowing it to reassociate with Gβγ and starting a new cycle.

The alpha subunit of the guanine nucleotide-binding protein $G_o$ ("o" for other) mediates signal transduction between a variety of receptors and effectors. Two forms of Go alpha subunit have been isolated from brain tissue libraries. These two forms, $G_{oA}$ alpha and $G_{oB}$ alpha (also referred to as $G_{oA}$ and $G_{oB}$), are the products of alternative splicing. $G_{oA}$ alpha transcripts are present in a variety of tissues but are most abundant in brain. The $G_{oB}$ alpha transcript is expressed at highest levels in brain and testis.

Specific GPCR screening assay techniques are known to the skilled artisan. For example, once candidate compounds are identified using the "generic" G protein-coupled receptor assay (i.e., an assay to select compounds that are agonists, partial agonists, or inverse agonists), further screening to confirm that the compounds have interacted at the receptor site is preferred For example, a compound identified by the "generic" assay may not bind to the receptor, but may instead merely "uncouple" the G protein from the intracellular domain.

$G_s$ stimulates the enzyme adenylyl cyclase. $G_i$ (and $G_z$ and $G_o$), on the other hand, inhibit this enzyme. Adenylyl cyclase catalyzes the conversion of ATP to cAMP; thus, constitutively activated GPCRs that couple the $G_s$ protein are associated with increased cellular levels of cAMP. On the other hand, constitutively activated GPCRs that couple $G_i$ (or $G_z$, $G_o$) protein are associated with decreased cellular levels of cAMP. See, generally, "Indirect Mechanisms of Synaptic Transmission," Chpt. 8, From Neuron To Brain (3rd Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein The reporter protein such as galactosidase or luciferase can then be detected using standard biochemical assays.

$G_q$ and $G_o$ are associated with activation of the enzyme phospholipase C, which in turn hydrolyzes the phospholipid $PIP_2$, releasing two intracellular messengers: diacycloglycerol (DAG) and inistol 1,4,5-triphoisphate ($IP_3$). Increased accumulation of $IP_3$ is associated with activation of $G_q$- and $G_o$-associated receptors. See, generally, "Indirect Mechanisms of Synaptic Transmission," Chpt. 8, From Neuron To Brain ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a $G_q$- or $G_o$-associated receptor (i.e., such a compound would decrease the levels of $IP_3$). $G_q$-associated receptors can also been examined using an AP1 reporter assay in that $G_q$-dependent phospholipase C causes activation of genes containing AP1 elements; thus, activated Gq-associated receptors will evidence an increase in the expression of such genes, whereby inverse agonists thereto will evidence a decrease in such expression, and agonists will evidence an increase in such expression. Commercially available assays for such detection are available.

The term "agent" or "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi or siRNA, asRNA, oligonucleotide, etc. An agent is any molecule that can be tested in an assay to identify the abukity of the agent to modulate the activity of presenilin. The agent can be in the form of a library of test compounds, such as a combinatorial or randomized library that provides a sufficient range of diversity. Agent are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that bind to, partially or totally block stimulation or enzymatic activity, decrease, prevent, delay activation, inactivate, desensitize, or down regulate the activity of presenilin, e.g., antagonists. Activators are agents that bind to, stimulate, increase, open, activate, facilitate, enhance activation or enzymatic activity, sensitize or up regulate the activity of presenilin, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of presenilin and then determining the functional effects on presenilin activity. Samples or assays comprising presenilin that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of presenilin relative to the control is about 80%, optionally 50% or 25-1%. Activation is achieved when the activity value of presenilin relative to the control is 110%, optionally 150%, optionally 200-500%, or 1000-3000% higher.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

"Determining the functional effect" refers to assaying for a compound that increases or decreases a parameter that is indirectly or directly under the influence of presenilin, e.g., measuring physical and chemical or phenotypic effects of e.g., presenilin interactions with a G-protein or β-APP. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of a substrate; changes in enzymatic activity, measurement of changes in protein levels of a polypeptide of the invention; measurement of RNA stability; G-protein binding; GPCR phosphorylation or dephosphorylation; tau phosphorylation or dephosphorylation, signal transduction, e.g., receptor-ligand interactions, second messenger concentrations (e.g., cAMP, $IP_3$, or intracellular $Ca^{2+}$); identification of downstream or reporter gene expression (CAT, luciferase, beta-gal, GFP and the like), e.g., via chemiluminescence, fluorescence, colorimetric reactions, antibody binding, inducible markers, and ligand binding assays. In addition, β-APP binding to presenilin and Aβ production can also be used as determinants of a functional effect on presenilin activity. The term "amyloid beta peptide" means amyloid beta peptides processed from the amyloid beta precursor protein (APP). The most common peptides include amyloid beta peptides 1-40, 1-42, 11-40 and 11-42. Other less prevalent amyloid beta peptide species are described as x-42, whereby x ranges from 2-10 and 12-17, and 1-y whereby y ranges from 24-39 and 41. For descriptive and technical purposes, "x" has a value of 2-17, and "y" has a value of 24 to 41.

Agents identified by methods provided herein may be administered therapeutically or prophylactically to treat diseases associated with amyloid fibril formation, aggregation or deposition, regardless of the clinical setting. The compounds of the invention may act to modulate the course of an amyloid related disease using any of the following mechanisms, such as, for example but not limited to: slowing the rate of amyloid fibril formation or deposition; lessening the degree of amyloid deposition; inhibiting, reducing, or preventing amyloid fibril formation; inhibiting amyloid induced inflammation; enhancing the clearance of amyloid from, for example, the brain; or protecting cells from amyloid induced (oligomers or fibrillar) toxicity.

"Modulation" of amyloid deposition includes both inhibition, as defined above, and enhancement of amyloid deposition or fibril formation. The term "modulating" is intended, therefore, to encompass prevention or stopping of amyloid formation or accumulation, inhibition or slowing down of further amyloid aggregation in a subject with ongoing amyloidosis, e.g., already having amyloid aggregates, and reducing or reversing of amyloid aggregates in a subject with ongoing amyloidosis; and enhancing amyloid deposition, e.g., increasing the rate or amount of amyloid deposition in vivo or in vitro. Amyloid-enhancing compounds may be useful in animal models of amyloidosis, for example, to make possible the development of amyloid deposits in animals in a shorter period of time or to increase amyloid deposits over a selected period of time. Amyloid-enhancing compounds may be useful in screening assays for compounds which inhibit amyloidosis in vivo, for example, in animal models, cellular assays and in vitro assays for amyloidosis. Such compounds may be used, for example, to provide faster or more sensitive assays for compounds. In some cases, amyloid enhancing compounds may also be administered for therapeutic purposes, e.g., to enhance the deposition of amyloid in the lumen rather than the wall of cerebral blood vessels to prevent CAA. Modulation of amyloid aggregation is determined relative to an untreated subject or relative to the treated subject prior to treatment.

"Inhibition" of amyloid deposition includes preventing or stopping of amyloid formation, e.g., fibrillogenesis, clearance of soluble Aβ from brain, inhibiting or slowing down of further amyloid deposition in a subject with amyloidosis, e.g., already having amyloid deposits, and reducing or reversing amyloid fibrillogenesis or deposits in a subject with ongoing amyloidosis. Inhibition of amyloid deposition is determined relative to an untreated subject, or relative to the treated subject prior to treatment, or, e.g., determined by clinically measurable improvement, e.g., or in the case of a subject with brain amyloidosis, e.g., an Alzheimer's or cerebral amyloid angiopathy subject, stabilization of cognitive function or prevention of a further decrease in cognitive function (i.e., preventing, slowing, or stopping disease progression), or improvement of parameters such as the concentration of Aβ or tau in the CSF.

As used herein, "treatment" of a subject includes the application or administration of a composition comprising an agent identified by a method of the invention to a subject, or application or administration of a composition of the invention to a cell or tissue from a subject, who has a amyloid-β related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination or a psychiatric evaluation. For example, the methods of the invention successfully treat a subject's dementia by slowing the rate of or extent of cognitive decline.

While Alzheimer's disease of the familial or the sporadic type is the major dementia found in the aging population, other types of dementia are also found. These include but are not limited to: the fronto-temporal degeneration associated with Pick's disease, vascular dementia, senile dementia of Lewy body type, dementia of Parkinsonism with frontal atrophy, progressive supranuclear palsy and corticobasal degeneration and Downs syndrome associated Alzheimers'. Plaque formation is also seen in the spongiform encephalopathies such as CJD, scrapie and BSE. The present invention is directed to treatment of such neurodegenerative diseases, particularly those involving neurotoxic protein plaques, eg. amyloid plaques.

Downs syndrome is a serious human disorder that occurs with an incidence of 1 in 800 live births. It is associated with the presence in affected individuals of an extra copy of chromosome 21 (trisomy 21). The β-amyloid precursor protein (β-APP) gene is encoded on chromosome 21, very close to the Down syndrome locus. All patients with Downs syndrome, if they survive beyond 40 years, develop Alzheimer's-like dementia and the deposition of Aβ in their brains. There is good reason, therefore, to propose that the over-production of Aβ is connected directly with the occurrence of the dementia in both AD and Downs syndrome. Therefore, the nature of the identification of therapeutic agents for the amelioration of the symptoms of AD will also be useful for the amelioration of the symptoms of Downs syndrome.

"Dementia" refers to a general mental deterioration due to organic or psychological factors; characterized by disorientation, impaired memory, judgment, and intellect, and a shallow labile affect. Dementia herein includes vascular dementia, ischemic vascular dementia (IVD), frontotemporal dementia (FTD), Lewy body dementia, Alzheimer's dementia, etc. The most common form of dementia among older people is Alzheimer's disease (AD).

The expressions "mild-moderate" or "early stage" AD are used as synonyms herein to refer to AD which is not advanced and wherein the signs or symptoms of disease are not severe. Subjects with mild-moderate or early stage AD can be identified by a skilled neurologist or clinician. In one embodiment, the subject with mild-moderate AD is identified using the Mini-Mental State Examination (MMSE). Herein, "moderate-severe" or "late stage" AD refer to AD which is advanced and the signs or symptoms of disease are pronounced. Such subjects can be identified by a skilled neurologist or clinician. Subjects with this form of AD may no longer respond to therapy with cholinesterase inhibitors, and my have a markedly reduced acetylcholine level. In one embodiment, the subject with moderate-severe AD is identified using the Mini-Mental State Examination (MMSE). "Familial AD" is an inherited form of AD caused by a genetic defect. A "symptom" of AD or dementia is any morbid phenomenon or departure from the normal in structure, function, or sensation, experienced by the subject and indicative of AD or dementia.

An agent may be administered therapeutically or prophylactically to treat diseases associated with amyloid fibril formation, aggregation or deposition. The agents of the invention may act to, ameliorate the course of fibril formation; inhibiting neurodegeneration or cellular toxicity induced by amyloid-β; inhibiting amyloid-β induced inflammation; enhancing the clearance of amyloid-β from the brain; or favoring greater catabolism of Aβ.

An agent may be effective in controlling amyloid-β deposition by acting directly on brain Aβ, e.g., by maintaining it in a non-fibrillar form or favoring its clearance from the brain. The compounds may slow down APP processing; may increase degradation of Aβ fibrils by macrophages or by neuronal cells; or may decrease Aβ production by activated microglia. These agents could also prevent Aβ in the brain from interacting with the cell surface and therefore prevent neurotoxicity, neurodegeneration, or inflammation.

An agent identified by a method provided herein may be used to treat Alzheimer's disease (e.g., sporadic or familial AD). The agent may also be used prophylactically or therapeutically to treat other clinical occurrences of amyloid-β deposition, such as in Down's syndrome individuals and in patients with cerebral amyloid angiopathy ("CAA"), hereditary cerebral hemorrhage, or early Alzheimer's disease.

The agent may be used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, V., et al. (1996) Proc. Natl. Acad. Sci. USA 93: 1314-1319; Askanas, V. et al. (1995) Current Opinion in Rheumatology 7: 486-496). Accordingly, agents identified by a method provided herein amy be used prophylactically or therapeutically in the treatment of disorders in which amyloid-β protein is abnormally deposited at non-neurological locations, such as treatment of EBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., Proc. Natl. Acad. Sci. USA 99(18), 11830-5 (2002)).

Accordingly, the invention relates generally to methods of treating or preventing an amyloid-related disease in a subject (preferably a human) comprising administering to the subject a therapeutic amount of an agent or compound identified by a method provided herein, such that amyloid fibril formation or deposition, neurodegeneration, or cellular toxicity is reduced or inhibited. In another embodiment, the invention relates to a method of treating or preventing an amyloid-related disease in a subject (preferably a human) comprising administering to the subject a therapeutic amount of a compound identified by a method described herein, such that cognitive function is improved or stabilized or further deterioration in cognitive function is prevented, slowed, or stopped in patients with brain amyloidosis, e.g., Alzheimer's disease, Down's syndrome or cerebral amyloid angiopathy. These compounds can also improve quality of daily living in these subjects.

Further, the present invention relates to pharmaceutical compositions comprising agents for the treatment of an amyloid-related disease, as well as methods of manufacturing such pharmaceutical compositions.

In general, the agents identified by methods provided herein may be prepared by any method known to the skilled artisan. The agents of the invention may be supplied in a solution with an appropriate solvent or in a solvent-free form (e.g., lyophilized). In another aspect of the invention, the agents and buffers necessary for carrying out the methods of the invention may be packaged as a kit. The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The therapeutic agent may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

To administer the therapeutic agent by other than parenteral administration, it may be necessary to coat the agent with, or co-administer the agent with, a material to prevent its inactivation. For example, the therapeutic agent may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7, 27 (1984)).

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

The therapeutic agent can be orally administered, for example, with an inert diluent or an assimilable edible carrier. The therapeutic agent and other ingredients may also be enclosed in a hard or soft shell gelatin capsule, compressed into tablets, or incorporated directly into the subject's diet. For oral therapeutic administration, the therapeutic agent may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic agent calculated to produce the desired therapeutic effect in association with the required pharmaceutical vehicle. The specification for the dosage unit forms of the invention are dictated by and directly dependent on (a) the unique characteristics of the therapeutic agent and the particular therapeutic effect to be achieved, and (b) the limitations inherent in the art of compounding such a therapeutic agent for the treatment of amyloid deposition in subjects.

The present invention therefore includes pharmaceutical formulations comprising agents identified by methods described herein, including pharmaceutically acceptable salts thereof, in pharmaceutically acceptable vehicles for aerosol, oral and parenteral administration. Also, the present invention includes such agents, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, an agent, and pharmaceutically acceptable salts thereof, may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired agent, or a salt thereof, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent, or a salt thereof, in a carrier which comprises water. A surfactant may be present which lowers the surface tension of the formulation sufficiently to result in the formation of droplets within the desired size range when subjected to nebulization.

Peroral compositions also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical-wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypiopyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emolients, emulsifiers, thickening agents, solvents and the like.

The working examples provided below are to illustrate, not limit, the disclosure. Various parameters of the scientific methods employed in these examples are described in detail below and provide guidance for practicing the disclosure in general.

EXAMPLES

Example 1 cDNAs for G-proteins $G\alpha_{oA}$ and $G\alpha_{oB}$ in pcDNA3 were purchased from UMR cDNA Resource Center, Rolla, Mo. Full-length human PS-1 and PS-2 cDNAs in pcDNA3 were cloned by PCR as already described. Tail-less constructs of PS-1 and PS-2 were constructed in pcDNA3 in which only the cytoplasmic domain of PS-1 or PS-2 immediately following the last TM-domain is deleted (this construct comprises of amino acids 1-430 of PS-1 and 1-410 of PS-2).

Cell culture: ES ($PS-1^{-/-}/PS-2^{-/-}$) cells were cultured according to published protocols.

Transfections: ES ($PS-1^{-/-}/PS-2^{-/-}$) were transiently transfected with 15 μg of pcDNA constructs of full-length human PS-1 or PS-2 and the cDNA of the desired G-proteins using the lipofectamine (Invitrogen) method. Briefly, the lipofectamine—DNA solution was be left at room temperature for 30 mins, mixed with enough serum-free medium and added to the cells. Cells were incubated for 5 h at 37° C. in a $CO_2$ incubator after which the medium was replenished with serum and cells harvested 12-24 hours after transfection.

Immunoprecipitations: 24 h after transfection, the culture medium was removed, and cells scraped in 200 μl of extraction buffer. Whole cell-extracts were made by sonication, using the solubilization conditions of Smine et al (50 mM HEPES/NaOH, pH 7.4, 1 mM EDTA, 1 mM DTT, 1% Triton X-100, 60 mM octylglycoside and protease inhibitors). 100 μg of each extract was immunoprecipitated using monoclonal antibodies to the large loop of PS-1 (MAB5232) or PS-2 (MA1-754). The immunoprecipitated proteins were next separated on 12% SDS PAGE and transferred to a membrane. Western blot hybridization against antibodies to the G protein $G_o$ (K-20, sc-387 from Santa Cruz Biotechnology, affinity purified; this polyclonal antibody recognizes both $G_{oA}$ and $G_{oB}$) was then carried out.

Western blot hybridizations: Immunoprecipitated proteins were boiled for 5 min in loading buffer (50 mM Tris, pH 6.8, 0.1 M DTT, 2% SDS, 0.1% bromophenol blue, 10% glycerol), separated electrophoretically on SDS-PAGE (12%) gels, and the proteins transferred onto nitrocellulose filters. Filters were incubated with the primary polyclonal rabbit G-protein antibodies followed by horse radish peroxidase-conjugated goat anti-rabbit IgG. Filter-bound peroxidase activity was detected by chemiluminescence.

Binding of G-protein $G_o$ to PS-1 ES ($PS-1^{-/-}/PS-2^{-/-}$) cells were transiently transfected with cDNA to full-length human PS-1 and the cDNA of the G-proteins $G_{oA}$ or $G_{oB}$ (UMR cDNA Resource Center, Rolla, Mo.). 24 h after transfection, whole cell-extracts were made by sonication, using the solubilization conditions of Smine et al (50 mM HEPES/NaOH, pH 7.4, 1 mM EDTA, 1 mM DTT, 1% Triton X-100, 60 mM octylglycoside and protease inhibitors). 100 μg of each extract was immunoprecipitated using monoclonal antibodies to the large loop, which is extracellular in the 7-TM model (Mab #5232, Chemicon, which was used in previous published work). The immunoprecipitated proteins were next separated on 12% SDS PAGE and transferred to a membrane. Western blot hybridization against antibodies to both, PS-1 and $G_o$ (K-20, sc-387 from Santa Cruz Biotechnology, affinity purified; this polyclonal antibody recognizes both $G_{oA}$ and $G_{oB}$) was then carried out.

Binding of G-protein $G_o$ to PS-2: ES ($PS-1^{-/-}/PS-2^{-/-}$) were transiently transfected with cDNA of full-length human PS-2 and the cDNA of the G-proteins $G_{oA}$ or $G_{oB}$ (UMR cDNA Resource Center, Rolla, Mo.). 24 h after transfection, whole cell-extracts were made by sonication, using the solubilization conditions of Smine et al (50 mM HEPES/NaOH, pH 7.4, 1 mM EDTA, 1 mM DTT, 1% Triton X-100, 60 mM octylglycoside and protease inhibitors). 100 μg of each extract was immunoprecipitated using mouse monoclonal antibodies to the large loop of PS-2 (MA1-754 from Affinity BioReagents). The immunoprecipitated proteins were next separated on 12% SDS PAGE and transferred to a membrane. Western blot hybridization against antibodies to both, PS-2 and $G_o$ was then carried out.

Pertussis Toxin Treatment: The PTx protomer was incubated with 10 mM DTT at 37° C. for 10 min to convert it to its enzymatically active form. 5 h after transfecting ES cells with PS-1 or PS-2 and the G-protein cDNAs, 500 ng/ml of activated PTx was added tot he cells in culture medium in the presence of 1 mM NAD, 2 mM $MgCl_2$ and 1 mM EDTA and the cells incubated at 37° C. in the presence of 5% $CO_2$ for 12 h. Cells were then harvested and examined for [$^{35}$S]GTPγS incorporation as described below.

GTPγS Binding: Cells were harvested and proteins solubilized by sonication in solublilization buffer (50 mM HEPES/NaOH pH 7.4, 1 mM EDTA, 1 mM DTT, 1% Triton-X100, 60 mM octylglycoside, 1× Protease inhibitor mix). 100 μg of protein was mixed with an equal volume of Buffer B (50 mM HEPES/NaOH pH 7.4, 40 μM GDP, 50 mM $MgCl_2$, 100 mM NaCl) in a volume of 200 μl. The reaction was started with 50 nM [$^{35}$S]GTPγS (1250 Ci/mmol) and incubation carried out for 60 min at RT after which the reaction was stopped by the addition of 20 μl of 10× Stopping buffer (100 mM Tris-Hcl, pH 8, 25 mM $MgCl_2$, 100 mM NaCl, 20 mM GTP. The sample was then immunoprecipitated with anti-PS-1 loop monoclonal antibody (5 μl). The antibody-protein complex was subjected to binding to Protein A/G agarose for 90 min at RT and washed twice with washing buffer 1 (50 mM HEPES, pH 7.4, 1 mM EDTA, pH 8.0, 1% Triton X-100 1× protease inhibitor mix, 150 mM NaCl and 60 mM octyl-β-D-glucopyranoside), and once with each of washing buffers 2 (50 mM HEPES, pH 7.4, 1 mM EDTA, pH 8.0, 0.5% Triton X-100, 1× protease inhibitor mix and 50 mM NaCl) and 3 (50 mM HEPES, pH 7.4, 1 mM EDTA, pH 8.0 and 1× protease inhibitor mix. The washed agarose beads were then suspended in scintillation fluid (CytoScint, ICN) (5 ml) and counted in a Beckman Coulter LS 6000 SC scintillation counter for 3 min.

When 100 μg of extract of ES (PS-1$^{-/-}$/PS-2$^{-/-}$) cells co-transfected with cDNAs for full-length human PS-1 and the G-protein $G\alpha_{oA}$ or $G\alpha_{oB}$ were immunoprecipitated with MAb to the large hydrophilic loop of PS-1, followed by Western blot hybridization with affinity purified polyclonal antibody to $G_o$ (which recognizes both isoforms, $G_{oA}$ and $G_{oB}$), only the PS-1/$G_{oA}$ co-transfected cells gave a robust signal for $G_o$ at ~45kDa (FIG. 1, lane 3), suggesting that $G_{oA}$, but not $G_{oB}$, binds to PS-1. Control untransfected cells or cells transfected with PS-1 alone did not show a $G_o$ band on Western blots when treated identically (FIG. 1).

Verification of the binding of G-protein $G_o$ to the cytoplasmic carboxyl terminus of PS-1. A tail-less construct of PS-1 was made in pcDNA3 in which only the cytoplasmic domain of PS-1 immediately following the last TM-domain is deleted (this construct comprises amino acids 1-430). This construct was used to transfect ES (PS-1$^{-/-}$/PS-2$^{-/-}$) cells. Tail-less PS-1 has been shown to integrate into the membrane and to be expressed at the cell surface. In an identical strategy to the one described above for full-length PS-1, ES (PS-1$^{-/-}$/PS-2$^{-/-}$) cells were transfected with cDNAs for tail-less PS-1 and the G-proteins $G_{oA}$ or $G_{oB}$. Cells extracts were then subjected to immunoprecipitation with PS-1 loop MAb #5232), separated on SDS PAGE and Western blotted with antibodies to $G_o$.

100 μg of extract of ES (PS-1$^{-/-}$/PS-2$^{-/-}$) cells co-transfected with cDNAs for tail-less PS-1 and the G-protein $G\alpha_{oA}$ or $G\alpha_{oB}$ were immunoprecipitated with MAb to the large hydrophilic loop of PS-1, followed by Western blot hybridization with affinity purified polyclonal antibody to $G_o$ (recognizes both isoforms, $G_{oA}$ and $G_{oB}$). Binding was detected (FIG. 1, lane 6) indicating that the carboxyl terminal 39 amino acids earlier identified to be the binding domain did not constitute the entire binding domain of PS-1 for $G_{oA}$. $G_{oB}$ showed no binding to tail-less PS-1 (FIG. 1, lane 7).

The results using the tail-less construct, which eliminated the major part of $G_{oA}$ binding to PS-1, show specificity for some PS-1:$G_{oA}$ binding to another region of PS-1 besides the PS-1 tail. They also rule out the possibility that $G_{oA}$ may have bound to other components of the PS-1 β-secretase complex, that may have co-immunoprecipitated with the PS-1 antibody.

Figure 3:
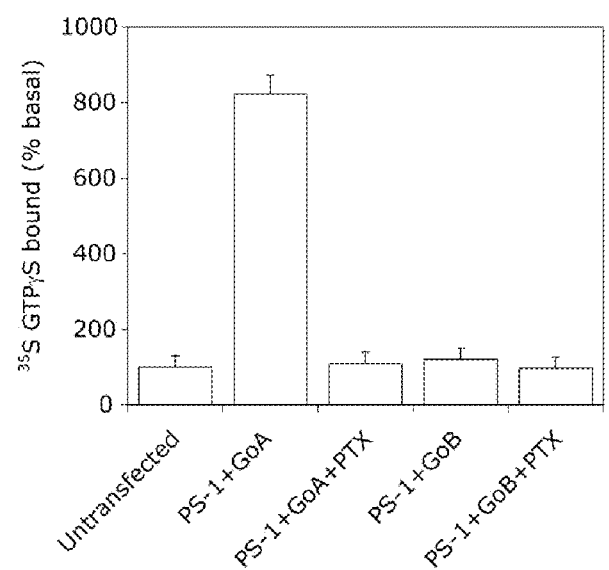
FIG. 3 involves an independent way of demonstrating $G_{oA}$ binding to PS-1. [$^{35}$S]-GTPγS, an analog of GTP, makes a covalent bond to the active site of a G-protein, that is blocked by a prior reaction with Pertussis toxin (PTx). In lane 2, there is shown an 8-fold increase in $^{35}$S-incorporation into $G_{oA}$ that is immunoprecipitated with antibody to PS-1, but not into $G_{oB}$ (lane 4). Therefore, PS-1 binds to $G_{oA}$(that has reacted with [$^{35}$S]-GTPγS to identify it as a G-protein (lane 2), but also to a lesser extent to $G_{oB}$ than to $G_{oA}$ (lane 4). The $^{35}$S bindings to $G_{oA}$ and $G_{oB}$ are blocked by prior treatment with PTx (lanes 3 and 5).

Additional studies were performed to elucidate the binding of G-protein $G_o$ to intact PS-2. The 39 amino acid PS-1 C-terminal region identified to be the binding domain is completely conserved in the C-terminal tail of PS-2. Accordingly, it was believed that the C-terminal domain of PS-2 would also bind $G\alpha_o$. As with PS-1, $G_o$ was shown to bind to PS-2, but with distinct differences. The $G_o$ antibody, which recognizes both $G_{oA}$ and $G_{oB}$, showed a doublet on Western blots of PS-2 immunoprecipitates of extracts of cells co-transfected with PS-2 and $G_{oA}$ as well as PS-2 and $G_{oB}$ cDNAs. The doublet presumably represents binding of both isoforms of $G_o$ to PS-2 (FIG. 3, lanes 2 and 4). In contrast, PS-1 did not bind to $G_{oB}$ (FIG. 1, lane 4) and only showed a single band on Western blots with the same $G_o$ antibody (FIG. 1, lane 3).

Figure 2:
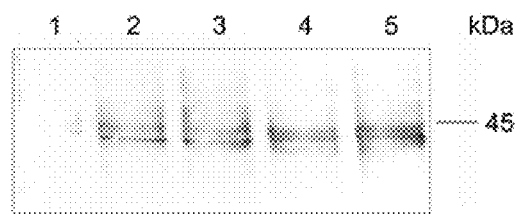
FIG. 2 shows a Western blot of a similar experiment to that of FIG. 1 but with PS-2 instead of PS-1. Lanes 2 and 4 show that tail-less PS-2, unlike tail-less PS-1, still binds $G_{oA}$ (and $G_{oB}$), and therefore that the binding sites for $G_{oA}$ and $G_{oB}$ are not confined to the C-terminal domain of PS-2, as is the case for PS-1 (FIG. 1) Lane 1 is untransfected ES (PS-1$^{-/-}$/PS-2$^{-/-}$). Lane 2 is PS-2+$G_{oA}$. Lane 3 is Tail-less PS-2+$G_{oA}$. Lane 4 is PS-2+$G_{oB}$. Lane 5 is Tail-less PS-2+$G_{oB}$.

The binding of G-protein $G_o$ to the cytoplasmic carboxyl terminus of PS-2 was investigated. As for PS-1, a tail-less construct of PS-2 was made in pcDNA3 in which only the cytoplasmic domain of PS-2 immediately following the last TM-domain was deleted (this construct comprised amino acids amino acids 1-410). This construct was used to transfect ES (PS-1$^{-/-}$/PS-2$^{-/-}$) cells and has been shown to integrate into the membrane and be expressed at the cell surface (FIG. 2). In an identical strategy to the one described above for full-length PS-1 and PS-2, ES (PS-1$^{-/-}$/PS-2$^{-/-}$) cells were transfected with cDNAs for tail-less PS-2 and the G-proteins $G_{oA}$ and $G_{oB}$. Cells extracts were then subjected to immunoprecipitation with PS-2 loop Mab #MA1-754), separated on SDS PAGE and Western blotted with antibodies to $G_o$.

When tail-less PS-2, co-expressed with $G_{oA}$ was immunoprecipitated with PS-2 MAb and Western blotted with anti $G_o$ antibody, as with results for PS-1, there was a decrease in band intensity, but the band was not totally absent. The intensity of the bands in the $G_{oB}$/PS-2 co-transfection sample, on the other hand, was unaltered for the tail-less sample suggesting that $G_{oB}$ binds PS-2 at an intracellular domain other than the carboxyl terminal tail FIG. 3, lanes 3 and 5). Therefore, PS-1 and PS-2 are discriminated not only by the $G_o$ isoforms that they bind to, but also the binding sites on the PS-1 and PS-2 that are not homologous to one another. It seems likely, therefore, that functional studies of PS-1 and PS-2 will give quite different results; i.e., PS-1 and PS-2 are not merely functionally redundant proteins.

Additional studies of PS mediated functional activation of $G\alpha_{oA}$ and $G\alpha_{oB}$ PS-1 and the G-proteins $G_{oA}$ and $G_{oB}$ were performed. Previous studies used GTP hydrolysis and GTPγS binding as one of several independent approaches to evaluate $G_o$ binding to the carboxyl terminus of PS-1. However, they carried out this assay with a synthesized peptide of residues 429-467 in the C-terminus of PS-1, along with three control peptides. The approach on the other hand was to evaluate the functional consequences of the binding of the G-proteins $G_{oA}$ and $G_{oB}$ to intact PS-1 and PS-2 in the co-transfected cell, by assaying for 35S-GTPγS incorporation in cell extracts.

Figure 4:
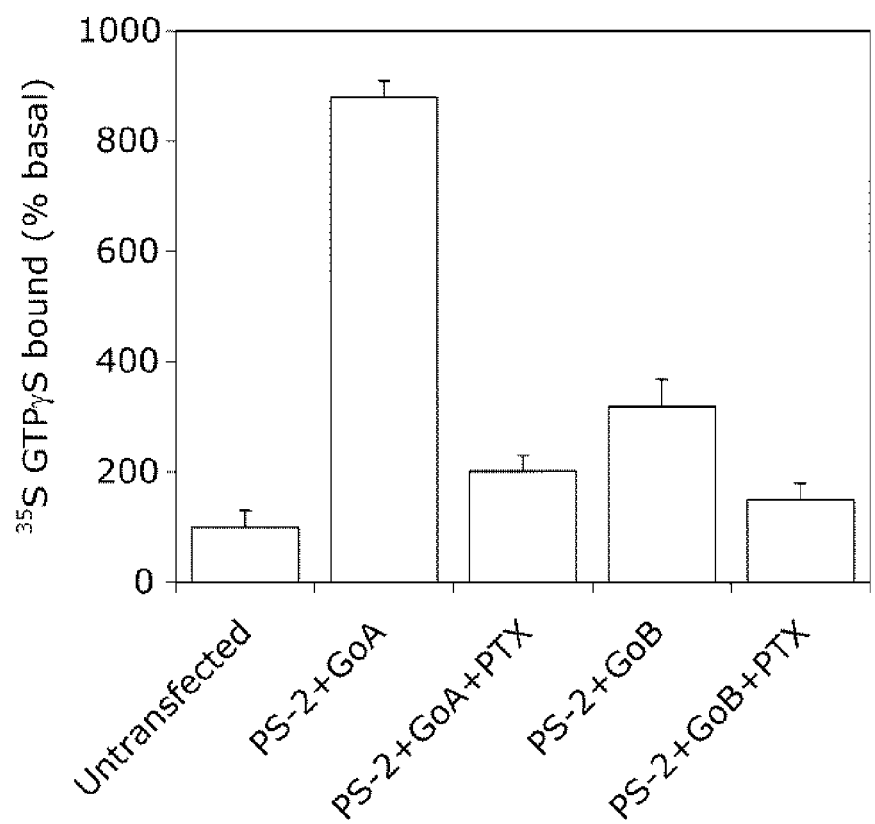
FIG. 4 is a graph depicting $^{35}$SGTPγS incorporation in extracts of ES cells transfected with cDNA for PS-2 and G-protein $G_{oA}$.

The $^{35}$S-GTPγS incorporation in extracts of ES cells that were co-transfected with cDNAs for PS-1 and the G-protein $G_{oA}$ was shown to be over 700% the value obtained for control untransfected ES (PS$^{-/-}$) cells (FIG. 4, lane 2). This increase was not seen when cells transfected with PS-1 and $G_{oA}$ cDNAs were first treated with PTx (FIG. 4, lane 3) showing an inhibition of function in the presence of the toxin. Cells transfected with cDNAs for PS-1 and $G_{oB}$ on the other hand did not show incorporation of $^{35}$S-GTPγS (FIG. 4 lane 4), consistent with previous results of a lack of binding of $G_{oB}$ to PS-1.

As with PS-1, PS-2 when co-expressed with $G_{oA}$ and assayed for $^{35}$S-GTPγS binding showed greater than 700% increase in $^{35}$S-GTPγS binding over untransfected control ES (PS$^{-/-}$) extracts (FIG. 4, lane 2). This was inhibited in the presence of PTx (FIG. 4, lane 3). Unlike the case for PS-1, $G_{oB}$ binding to PS-2 does give an increase in $^{35}$S-GTPγS incorporation. This novel finding is consistent with other data provided herein indicating that $G_{oB}$ binds to PS-2 but not PS-1. The increase in $^{35}$S-GTPγS incorporation is less than that observed for $G_{oA}$ (~300%) (FIG. 4, lane 4). This increase is inhibited in the presence of PTx. The results shown in FIG. 4 are representative of at least 3 independent experiments.

Example 2

ES PS double-null cells were cultured and plated overnight. The cells were transfected with a pcDNA3 construct of full-length human β-APP cDNA using lipofectamine (Invitrogen) according to the manufacturer's protocols. DAMI cells were cultured and transfected either with pcDNA3 or with a pcDNA3 construct of full-length human PS-1 or PS-2 cDNA.

Affinity-purified polyclonal rabbit anti-PTyr antibodies (Maher et al., 1985) were used in Western blots and were a kind gift from Dr. Elena Pasquale. A mouse monoclonal anti-PTyr antibody (4G10; Upstate Biotechnology, Lake Placid, N.Y.) was used in ELISA analyses. Mouse monoclonal antibody to human pp60c-src (Anti-Src, clone GD11) and rabbit polyclonal antibody to Lyn (Anti-Lyn) were purchased from Upstate Biotechnology. Rabbit polyclonal antibody to Fyn (Anti-Fyn, sc-16) was purchased from Santa Cruz Biotechnology, Santa Cruz, Calif. Primary rat anti-human PS-1 monoclonal antibody MAb #1563 directed to the N-terminal domain of PS-1 was purchased from Chemicon International, Temecula, Calif. It was raised to a fusion protein antigen containing part of the N-terminal domain of human PS-1 (residues 21-80) fused to GST. Primary mouse monoclonal antibody MAb #348 to the human β-APP extracellular domain was purchased from Chemicon International.

Fluorescein isothiocyanate (FITC)-conjugated affinity purified goat anti-rat IgG and tetramethylrhodamine B isothiocyanate (TRITC)-conjugated affinity purified donkey anti-mouse IgG secondary antibodies were purchased from Jackson ImmunoResearch, West Grove, Pa. Immunofluorescence labeling Transfected and untransfected DAMI cells were fixed with 4% paraformaldehyde in PBS for 10 mins and used without permeabilization. Cells were labeled in suspension with antisera to PS-1 (1:200 dilution), and β-APP (1:500 dilution) in PBS containing 1% BSA for 30 min at room temperature. After washing with PBS three times by centrifugation, the cells were resuspended in 1% BSA/PBS and incubated with appropriate fluorescent secondary antibodies. Incubation was carried out at room temperature for 20 min, after which the cells were washed with PBS and mounted onto slides in the presence of mounting medium (Vector Laboratories, Burlingame, Calif.).

Immunofluorescent microscopy was performed using oil immersion with a X60 objective lens. The slides were viewed using fluorescein isothiocyanate and tetramethylrhodamine B isothiocyanate filters and a Zeiss Photoscope III instrument, or with Nomarski optics.

N-terminal domains of PS-1 and PS-2 were obtained by PCR and cloned into the Tth 111 I and Xho-1 sites of the FLAG expression vector (Scientific Imaging Systems, IBI 13100) to produce a fusion protein with FLAG attached at the N-terminus of either the PS-1- or 2 N-terminal domains. The two FLAG-fusion proteins were grown separately in DH5α bacteria and affinity purified according to the manufacturer's protocols. The purified recombinant proteins were checked by Western blots using antibodies to both FLAG and either the N-terminal domain of PS-1 or PS-2.

DAMI:ES cells: Equal numbers ($0.5\times10^6$/ml) of β-APP 695 (Selkoe and Podlisny, 2002)-transfected ES double-null cells and PS-1 transfected DAMI cells were co-cultured at 37° C. for various times between 0-20 mins.

All experiments after those in FIG. 7 (with the exception of FIG. 9a, Panel 4) were carried out with appropriately transfected DAMI cells only. Equal numbers ($0.5\times10^6$/ml) of β-APP-transfected DAMI cells and either PS-1- or PS-2-transfected DAMI cells were mixed gently at room temperature, exactly as described (Dewji and Singer, 1998). In control experiments, DAMI cells transfected with pcDNA3 alone were substituted for the β-APP transfected cells.

At several times between 0 and 20 min after mixing, an aliquot of each cell mixture was rapidly centrifuged, the culture medium was removed, and the cell pellet was suspended in 200 μl of extraction buffer (50 mM Tris, pH 8.0/150 mM NaCl/0.5% Nonidet-P40) containing protease inhibitors (1 mM 4-(2-aminoethyl)benzene sulfonyl fluoride hydrochloride (AEBSF)/1 μg/ml antipain/0.1 μg/ml pepstatin A/0.1 μg/ml leupeptin) and the phosphatase inhibitor sodium orthovanadate (0.1 mM). The mixture was sonicated with three bursts of 20 sec duration and then centrifuged. These extract supernatants were then used for Western blot and ELISA analyses as described below.

Assays for Src family of protein tyrosine kinases in cell extracts were performed. The substrate peptide {[Lys19] cdc2 (6-20)-NH2} and control peptides {[Lys19Ser14Va112] cdc2 (6-20)} and {[Lys19Phe15] cdc2 (6-20)} were purchased from Upstate Biotechnology Inc. Src kinase activity was measured in extracts of transfected DAMI cells (either β-APP- or pcDNA3-transfected) mixed with PS-1-transfected cells; and with β-APP- or pcDNA3-transfected cells mixed with PS-2-transfected cells, using all three peptides. Controls included experiments carried out using no substrate in the reaction mixture.

The substrate peptide (1.5 mM in 10 μl), Src kinase reaction buffer (100 mM Tris-HCl, pH 7.2, 125 mM $MgCl_2$, 25 mM $MnCl_2$, 2 mM EGTA, 0.25 mM sodium orthovanadate, 2 mM DTT) (10 μl), Src kinase (2-20 U of purified enzyme per assay or 10-200 μg protein lysate in 10 μl and [γ-$^{32}$P]ATP (NEN Dupont, Boston, Mass.) diluted with $Mn^{2+}$/ATP cocktail (10 μl), were incubated for 15-20 min at 30° C.

Aliquots of the extract supernatants described above (100 μg protein/lane) were boiled for 5 min in loading buffer (50 mM Tris, pH 6.8, 0.1 M DTT, 2% SDS, 0.1% bromophenol blue, 10% glycerol), separated electrophoretically on SDS-PAGE (10%) gels, and the proteins transferred onto nitrocellulose filters. Filters were incubated with the primary polyclonal rabbit anti-PTyr antibodies followed by the horse radish peroxidase-conjugated goat anti-rabbit IgG. Filter-bound peroxidase activity was detected by chemiluminescence.

Cell lysates were prepared in extraction buffer and clarified by micro-centrifugation at 4° C. for 15 mins.

Extracts were incubated with 4 μg antibodies specific for either c-Src, Lyn or Fyn followed by protein-A or G sepharose (40 μl of slurry). The antigen antibody-protein-A (or -G) sepharose complex was washed three times in RIPA (50 mM Tris-HCl, pH 7.2, 150 mM NaCl, 1% Triton X-100, 1% Na deoxycholate, 0.1% SDS, 1% trasylol, 25 μM leupeptin) containing 300 mM NaCl, once with RIPA containing 10 mM NaCl, twice with 40 mM Tris-HCl, pH 7.2 and once with kinase buffer containing 25 mM HEPES, pH 6.9, 3 mM $MnCl_2$ and 200 μM sodium orthovanadate.

Reactions were performed according to published protocols (Zisch et al., 1998) in 40 μl kinase buffer (25 mM Hepes, pH 6.9, 3 mM $MnCl_2$ and 200 μM sodium orthovanadate) containing 5 μCi [g32P] ATP (3000 Ci/mmol) for 30 min at 37° C. The reaction beads were washed three times with kinase buffer and resuspended in 75 μl SDS gel loading buffer (250 mM Tris-HCl, pH 6.8, 4% SDS, 10% 2-mercaptoethanol, 0.02% bromophenol blue and 75% glycerol). Autophosphorylation reactions were subjected to SDS-PAGE followed by transfer of proteins onto PVDF membranes and autoradiography.

ELISAs Protein tyrosine kinase activity was measured by an Enzyme Linked Immunosorbent Assay (ELISA) using a tyrosine kinase assay kit (Upstate Biotechnology). A biotinylated substrate peptide containing tandem repeats of Poly (Glu4-Tyr) was incubated with supernatants of extracts of transfected cells mixed for different times (20 µg protein/well) in the presence of non-radioactive ATP and a $Mn^{2+}/Mg^{2+}$ co-factor cocktail according to the manufacturer's protocols. A phosphotyrosine specific mouse monoclonal antibody (4G10) conjugated to horseradish peroxidase was used to detect the phosphorylated substrate by ELISA.

Absence of cell surface expression of β-APP in untransfected and PS-1-transfected DAMI cells. Because the initial set of studies depends on the proposition that DAMI cells, after transfection with PS-1, continue to express only negligible amounts of β-APP on their surface, the following experiments were first carried out. Both untransfected and PS-1-transfected DAMI cells in the fixed but impermeable state were doubly immunofluorescently labeled for β-APP and PS-1. Untransfected fixed impermeable DAMI cells, as previously shown (Querfurth and Selkoe, 1994), do not express significant amounts of β-APP at the cell surface (FIG. 5a, Panel 2), whereas DAMI cells transfected with a pcDNA3 construct of β-APP show substantial cell-surface expression in fixed impermeable cells (FIG. 5b, Panel 2). FIGS. 5a and b, Panels 1 show, however, that untransfected fixed impermeable DAMI cells do express endogenous cell-surface PS-1. In FIG. 5c, Panel 1, this cell-surface expression of PS-1 is increased in fixed impermeable PS-1-transfected cells. FIG. 5c, Panel 2, shows that transfecting DAMI cells with PS-1 does not significantly increase the cell-surface expression of β-APP over the negligible levels seen in untransfected cells (FIG. 5a, Panel 2). FIG. 5d, Panel 2, shows cell-surface expression of β-APP in ES double-null fixed impermeable cells transfected with β-APP, but not PS-1 expression (FIG. 5d, Panel 1).

With untransfected, fixed impermeable ES double-null cells, there is, as expected, no labeling for cell-surface PS-1 (FIG. 5e, Panel 1), but a small amount of surface expression of endogenous β-APP (FIG. 5e, Panel 2). These results confirm that in interactions of β-APP-transfected ES double-null cells and PS-transfected DAMI cells, only the ES cells express cell-surface β-APP, and no PS; while only the PS-transfected DAMI cells express PS, and no β-APP, at the cell-surface. If a β-APP:PS interaction occurs after cell mixing, it can therefore only be the result of a cell-cell interaction.

Figure 6:
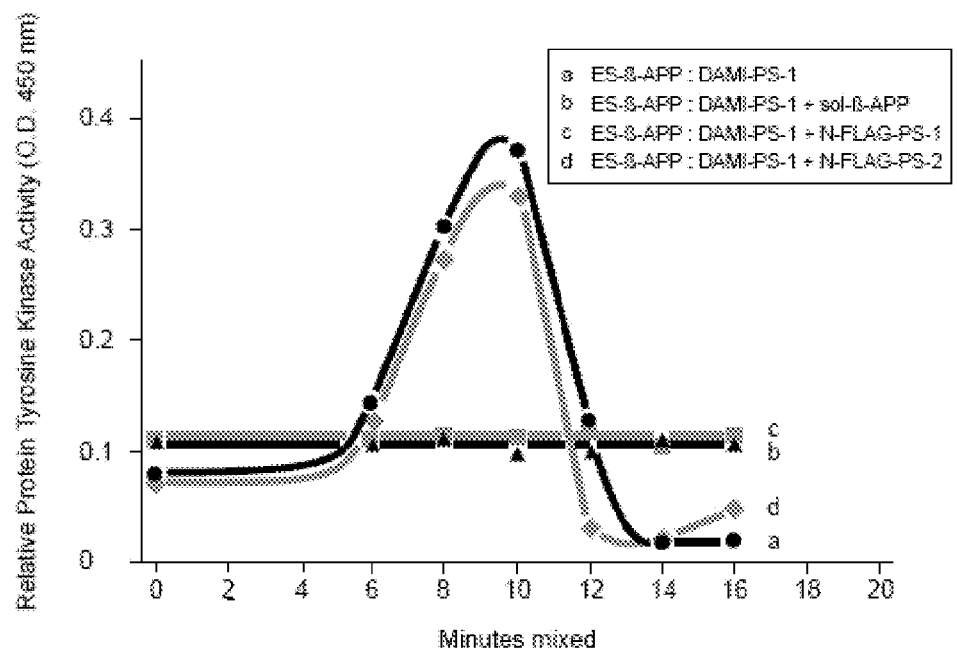
FIG. 6 shows that within minutes after mixing β-APP-only expressing transfected ES cells with PS-1 only expressing transfected DAMI cells, a transient protein tyrosine phosphorylation process arises in the mixed cell culture, as detected by ELISA analyses of the cell extracts. This activity peaked at ~8-10 mins after mixing (a). The same experiment carried out in the presence of 25 μg purified soluble β-APP (b) or 25 μg purified peptide of N-terminal domain of PS-1 fused to FLAG (c) showed none of the increases observed in (a). The addition of 25 μg of purified peptide of the non-specific N-terminal domain of PS-2 fused to FLAG (d), however, resulted in very similar transient increases in protein tyrosine kinase activity to (a).

Also provided herein are data indicating that specific β-APP:PS intercellular signaling results in an increase in tyrosine kinase activity. ES double-null cells transfected with β-APP were mixed with DAMI cells transfected with PS-1, and were co-cultured for various times between 0-20 min, using cell densities that ensured cell-cell contact. ELISA assays were then carried out on cell extracts to measure protein tyrosine kinase activity. FIG. 6 line "a" shows that these co-cultures produced a rapid and transient increase in protein tyrosine kinase activity similar in extent and kinetics to those previously described when PS-1-transfected DAMI cells were mixed with β-APP-transfected DAMI cells (Dewji and Singer, 1998). When the same interaction as in FIG. 6 line "a" was carried out in the presence of 25 µg of purified baculovirus-derived soluble β-APP (extra-cellular domain of β-APP) (FIG. 6 line "b") or 25 µg of fusion peptide of the FLAG reporter fused to the N-terminal domain of PS-1 (FIG. 6 line "c"), no increase in protein tyrosine kinase activity resulted. On the other hand, the same β-APP:PS-1 co-cultures in the presence 25 µg of FLAG-PS-2 N-terminal domain fusion peptide did not inhibit PTyr formation (FIG. 6 line "d"). These results clearly establish several points: 1) Soluble β-APP itself does not activate the PS-1-transfected DAMI cells to exhibit tyrosine kinase activity; the intact β-APP in the transfected ES cell membrane is required. On the contrary, the soluble β-APP inhibits the activity produced by the membrane-bound β-APP, demonstrating that membrane-bound β-APP is specifically involved in the activation; 2) the N-terminal domain of PS-1 is itself incapable of activating the β-APP-transfected cell to exhibit tyrosine kinase activity. The intact PS-1 molecule in its DAMI cell membrane is required. But the N-terminal domain of PS-1 (but not PS-2) inhibits the activation of the co-culture, showing that membrane-bound PS-1 on the PS-1-transfected DAMI cell is also specifically involved in the interaction; 3) The protein nature of the inhibitors, soluble β-APP and the FLAG—fusion protein of the N-terminal domain of PS-1, assures their impenetrability of the cell membranes of living DAMI and ES cells, and therefore demonstrates that it is only the exterior domains of the cell-surface β-APP and PS-1 that are involved in generating the signaling event (i.e., the signaling is of the juxtacrine type). These results provide compelling evidence that establish that a juxtacrine interaction between β-APP and PS can occur.

Furthermore, this demonstration that the N-terminal domain of PS-1 is exposed at the extracellular surface is consistent with the 7-TM topography of the PS proteins, but is contrary to the prediction of the 8-TM model, which positions the N-terminal domain of PS intra-cellularly.

Additional data provided herein indicate that β-APP:PS-1 and β-APP:PS-2 intercellular signaling can be mediated by members of the Src family of tyrosine kinases. The increases in PTyr modification that are a consequence of β-APP:PS intercellular binding involved one or more protein tyrosine kinases that need to be identified. Since neither β-APP nor the PS proteins contain such a kinase active site, an indirect activity of the cytoplasmic domains of these proteins, such as the direct or indirect binding of a cytoplasmic tyrosine kinase to one of these domains, may be involved in the downstream signal. Since several cytoplasmic tyrosine kinases have been identified within the Src gene family, Src family protein tyrosine kinases were assayed in cell extracts of mixed transfected cells using the substrate peptide [lys19]cdc2(6-20)-NH$_2$ (KVEKIGTYGVVKK (SEQ ID NO:4)). This peptide, with Tyr 19 in cdc2(6-20) replaced by lys, has been shown to be an efficient substrate for the Src family kinases. All Src family kinases tested, including v-Src and c-Src, c-Yes, Lck, Lyn and Fyn, demonstrate strong activity towards this substrate. Two control peptides were also used: In the first peptide, [lys19ser14val12]cdc2(6-20)NH$_2$(KVEKIGVGSYGV-VKK (SEQ ID NO:5)), glu12 and thr14 were replaced by val and ser, respectively, causing a significant decrease in efficiency of the resulting peptide to serve as a substrate for the Src family tyrosine kinases. The other peptide, [lys19phe15] cdc2(6-20)NH2 (KVEKIGEGTFGVVKK (SEQ ID NO:6)) should not be phosphorylated by tyrosine kinases but did contain a potential target for ser/thr kinases (thr 14).

The results of Src family kinase activity measurements in extracts of co-cultures of β-APP-transfected DAMI cells with PS-1-transfected DAMI cells evoking β-APP:PS-1 interactions, and for the corresponding control lacking β-APP (pcDNA3:PS-1), are shown in FIGS. 7a and b. Similar results for transfected DAMI cell mixtures evoking β-APP:PS-2 interactions, and extracts of control pcDNA3:PS-2 mixed transfected DAMI cells, using these three peptides are shown in FIGS. 7c and d. For each β-APP:PS cell mixture, where [lys19]cdc2(6-20)NH2 was u sed as the Src family kinase substrate, the temporal course of increased activity compared to control peptides were obtained that paralleled ELISA results for tyrosine kinase activity. For the β-APP:PS-1 interaction (FIG. 7a), Src family kinase activity peaked at 8 minutes and returned to baseline levels by 12 minutes confirming previous ELISA results for tyrosine kinase activity as a function of time after cell mixing. No significant increase could be observed when the same substrate was used for the control pcDNA3:PS-1 (FIG. 7b) mixed cells. For the cell mixtures evoking β-APP:PS-2 interactions (FIG. 7c), as for the tyrosine kinase ELISA results, two clear peaks of activity were observed with substrate peptide [lys19]cdc2(6-20)NH$_2$, at 9 and 16 minutes after mixing.

For the corresponding control lacking β-APP, pcDNA3:PS-2 (FIG. 7d), no significant increases of Src kinase activity over background were observed. These results suggest that the increases in tyrosine kinase activity previously observed for β-APP- with PS-1-transfected cell mixtures, or β-APP- with PS-2-transfected cell mixtures, involve one or more members of the Src tyrosine kinase family.

Figure 8A:
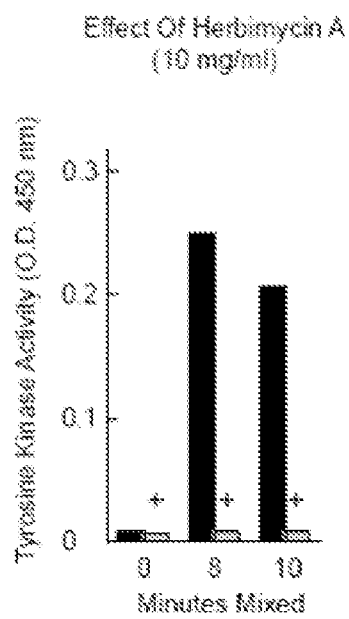
Figure 8A:
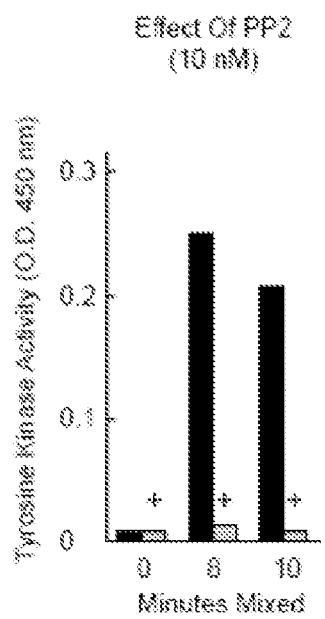

Inhibition of tyrosine kinase activity in the presence of specific inhibitors of Src family kinases and tyrosine kinase. The involvement of the Src kinase family in β-APP:PS intercellular signaling was further confirmed with ELISAs of extracts of β-APP:PS-1 mixed cell interactions carried out in the presence or absence of specific inhibitors of tyrosine kinase (herbimycin A) and Src family kinases (PP2). FIG. 8a demonstrates that in the presence of 10 μg/ml herbimycin A, the increase in tyrosine kinase activity at 8-10 mins after mixing β-APP-transfected DAMI cells with PS-1-transfected DAMI cells is completely inhibited. The same experiment carried out in the presence of 10 nM PP2 (FIG. 8b) similarly showed the inhibition of tyrosine kinase activity.

Figure 9A:
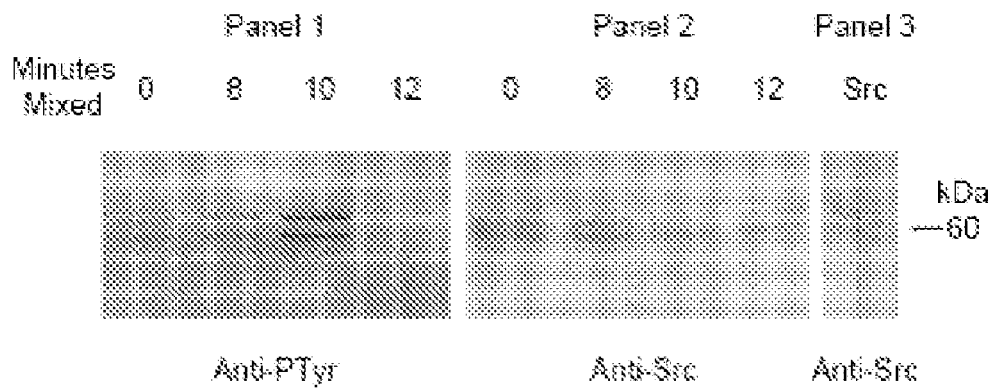
FIG. 9A-B shows β-APP:PS-1 intercellular interaction: C-Src activity in extracts of mixed cells. a. Western Immunoblot. β-APP:PS-1 interactions with mixtures of separately transfected DAMI cells. Western immunoblot with primary anti-PTyr polyclonal antibodies (Panel 1) and anti-pp60c-src monoclonal antibodies (Panel 2) from the same experiment in which β-APP-transfected DAMI cells were mixed with PS-1-transfected DAMI cells for 0-12 mins. Panel 3: Antibody labeling of control pp60c-src protein with the pp60c-src antibodies. Panel 4: Western immunoblots with primary anti-PTyr antibodies, as in Panel 1, from experiments in which β-APP-transfected ES double-null cells were interacted with PS-1-transfected DAMI cells. b. Autoradiograph of in-vitro phosphorylated proteins. Extracts of separately transfected β-APP and PS-1 DAMI cell mixtures at 0-12 mins after mixing were first immunoprecipitated with antibodies to c-Src and then phosphorylated in vitro with γ32P-ATP. Autophosphorylation reactions were subjected to SDS-PAGE followed by autoradiography.
Figure 9A:
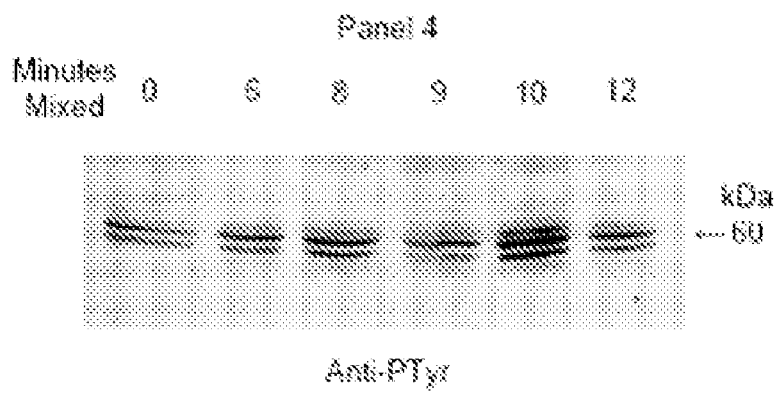

Additional data related to the involvement of c-Src in β-APP:PS-1 intercellular signaling is provided below. In order to determine the identity of the Src family member(s) involved in the β-APP:PS-1 intercellular signaling, we began by investigating pp60c-Src. Two main protein bands of apparent molecular weights 58 and 60 kDa, a doublet similar in size to c-Src, underwent transient PTyr modification in this juxtacrine interaction. When extracts of mixtures of PS-1-transfected DAMI cells with β-APP-transfected DAMI cells were subjected to SDS16 PAGE and immunoblotting with either anti-PTyr or anti-c-Src antibodies, both antibodies reacted with the same two bands (FIG. 9a, Panels 1-3). Panel 1 of this figure immunoblotted with anti-PTyr antibodies shows transient increases in tyrosine phosphorylation of the protein bands with a maximum at 8-10 mins after cell mixing. In Panel 2 the same extracts immunoblotted with the c-Src antibody show no variation with time, indicating that the c-Src protein concentration remains unchanged during the increase in its PTyr levels. An important observation was that when ES double-null cells transfected with β-APP (therefore expressing only β-APP, but no PS-1 or 2) were mixed with DAMI cells transfected with PS-1 (therefore expressing only PS-1, but no cell surface β-APP), the p60 c-Src proteins plus one or two additional proteins underwent transient increases in PTyr modification at similar times after mixing (FIG. 9a, Panel 4) that were seen with the β-APP-transfected DAMI cells mixed with PS-1-transfected DAMI cells (FIG. 9a, Panel 1). The PTyr modification results were therefore associated with PS-1 and not the cell type that expressed it (see below for PS-2).

In order to test further whether c-Src was the member of the tyrosine kinase family that underwent transient tyrosine phosphorylation in the β-APP:PS-1 interaction, experiments were carried out (autophosphorylation) in which the extracts of the mixed transfected DAMI cells taken at different times after mixing were treated with anti-c-src antibodies, followed by protein-G sepharose beads. To the beads was then added γ$^{32}$PATP; subsequently the proteins were solubilized from the beads, and subjected to SDS17 PAGE and autoradiography. The results in FIG. 9b demonstrate that several transient bands appear that are maximally phosphorylated at 8-10 min after cell mixing, a time course corresponding to the appearance of PTyr in the analogous extracts (FIG. 9a, Panel 1). Prominent among these bands is one doublet corresponding to c-Src, confirming that c-Src is activated transiently in the β-APP:PS-1 intercellular interaction.

Figure 9B:
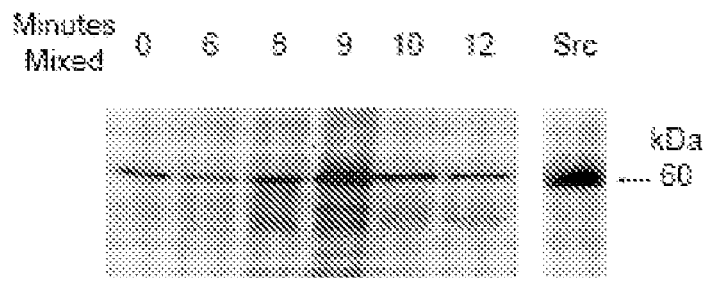

The identities of the other phosphorylated bands in FIG. 9b are not known. Not all of them are necessarily due to tyrosine phosphorylation; some serine or threonine kinases might have been bound to the c-Src that was immuno-reacted with specific anti-pc-Src. Involvement of Lyn but not Fyn downstream of β-APP:PS-2 intercellular signaling. When β-APP:PS-2 intercellular interactions were carried out with mixtures of appropriately transfected DAMI cells, an entirely different set of proteins was PTyr modified than for the β-APP:PS-1 system. Although bands were detected by the PTyr antibody that were present at 50-66 kDa, these did not correspond to c-Src on Western blots (FIGS. 11a, Panel 1). Furthermore, when extracts of β-APP:PS-2 mixed cells were first immunoprecipitated with c-Src antibodies and the immunoprecipitates were then autophosphorylated in vitro, no significant increases in phosphorylation at the earlier time points (8-10 mins after mixing) were seen (FIG. 10b).

Figure 10A:
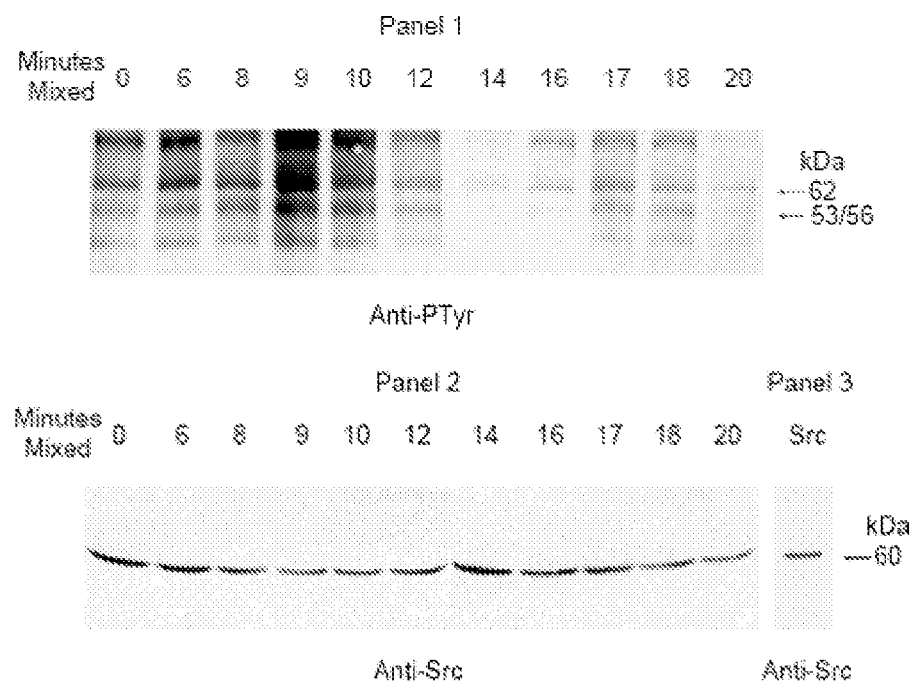
FIG. 10A-B shows β-APP:PS-2 intercellular interaction: C-Src activity in extracts of mixed cells. a. Western Immunoblot. β-APP:PS-2 interaction in extracts of separately transfected and mixed DAMI cells as a function of time after mixing. Panels 1 and 2: Same as FIG. 9a except that PS-2-transfected DAMI cells replaced PS-1-transfected cells in the intercellular interaction with β-APP and cells were mixed from 1-20 mins. b. Autoradiograph of in-vitro phosphorylated proteins. Same extracts as in part a. Same as 5b except that PS-2-transfected DAMI cells replaced PS-1-transfected DAMI cells in the intercellular interaction with β-APP.
Figure 10B:
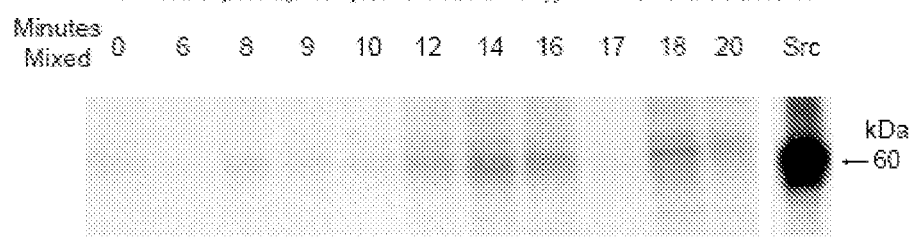
Figure 11A:
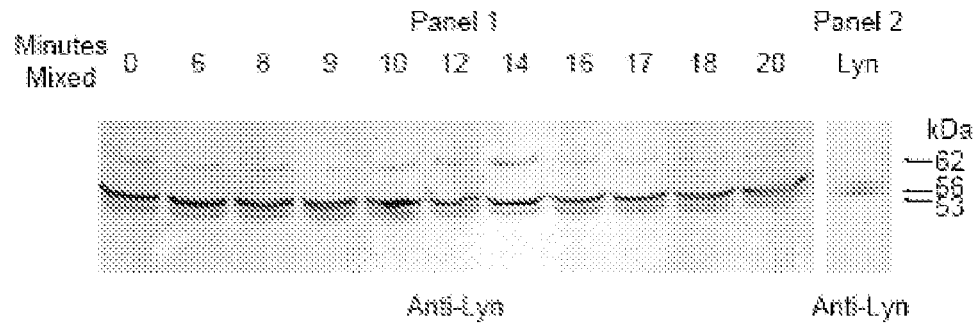
FIG. 11A-D shows β-APP:PS-2 intercellular interaction: Activity of Lyn and Fyn in extracts of mixed cells. a and b. Western Immunoblots: β-APP:PS-2 interaction. Western immunoblot with primary anti-Lyn polyclonal antibodies (a, Panel 1) and anti-Fyn polyclonal antibodies (b, Panel 1) from the same experiment in which β-APP-transfected DAMI cells were mixed with PS-2-transfected DAMI cells for 0-20 mins and extracts made. No change with time in concentration of either Lyn or Fyn protein was observed. Panel 2: Antibody labeling of control Lyn (a) and Fyn (b) protein with their respective antibodies. c and d. Autoradiograph of in-vitro phosphorylated proteins: β-APP:PS-2 interaction. Extracts of mixtures of β-APP and PS-2 mixed transfected cells at 0-20 mins after mixing were first immunoprecipitated with antibodies to Lyn (c) or Fyn (d) and then phosphorylated in vitro with γ32P-ATP. Autophosphorylation reaction products were subjected to SDS-PAGE followed by autoradiography.

At later time points however, c-Src could apparently be phosphorylated in these samples indicating that it contributes to increases identified in the second later peak of β-APP:PS-2 signaling (FIG. 10b). The possible involvement of other members of the Src kinase family was investigated with molecular weights in the 53-59 kDa range other than c-Src. Lyn (Mwt 53/56 kDa) and Fyn (Mwt 59 kDa) were two candidate Src kinases that were examined.

Figure 11B:
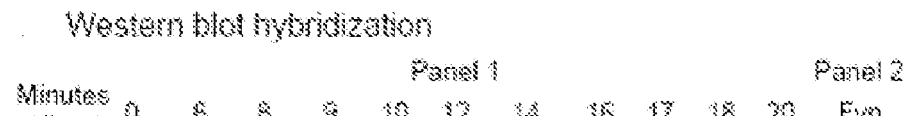
Figure 11C:
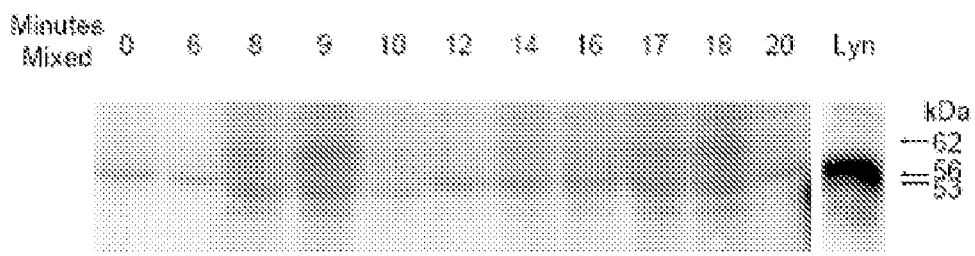
Figure 11D:
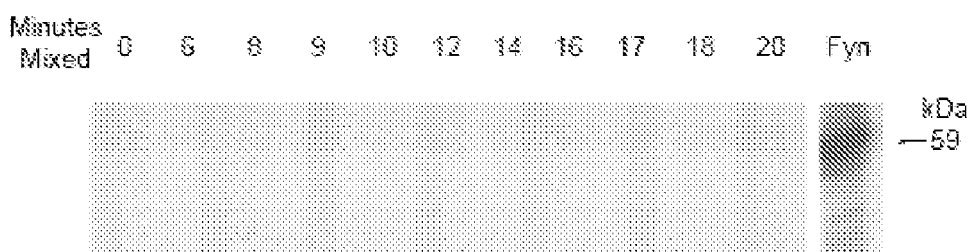

Results of Western blot hybridization with anti-Lyn antibodies in FIG. 11a show that Lyn protein concentrations do not change when β-APP:PS-2 intercellular interactions are carried out, but after immunoprecipitation of the extracts with anti-Lyn antibodies and in vitro autophosphorylation of the precipitates, a transient phosphorylation of Lyn with peaks of activity at 8-9 and 17-18 min is observed, along with other phosphorylated bands (FIG. 11c). Lyn undergoes transient phosphorylation in a pattern that is similar to the PTyr increases seen on Western blots and ELISAs for β-APP:PS-2 interaction (FIG. 11c). Fyn, on the other hand, shows no autophosphorylation in-vitro in the same extracts after immunoprecipitation with anti-Fyn antibodies (FIG. 11d), nor any change in its concentration with time (FIG. 11b).

Example 3

The following data demonstrates G-protein binding to endogenous PS-1 and PS-2 in extracts of mouse frontal cortex. A 20% homogenate of WT mouse frontal was made in GTPγS solublization/extraction buffer [50 mM HEPES/NaOH pH 7.4, 1 mM EDTA, 1 mM DTT, 1% Triton-X100, 60 mM octylglycoside, 1× Protease inhibitor mix (1 uM phenylmethylsulfonylflouride, 1 ug/mL antipain, 0.1 ug/mL pepstatin A, 0.1 ug/mL leupeptin)]. Measurements of [$^{35}$S]GTPγS binding were performed on Untreated, PTX treated; and PS-1 and PS-2 immuno-depleted extracts.

For untreated samples, 100 μg of extract was brought up to 100 uL in GTPγS solublization/extraction buffer and mixed with an equal volume of GTPγS Buffer B (50 mM HEPES/NaOH pH 7.4, 40 μM GDP, 50 mM MgCl$_2$, 100 mM NaCl) for a total volume of 200 μL. The reaction was started with 50 nM [$^{35}$S] GTPγS (1250 Ci/mMol; Perkin Elmer) and incubated at RT for 60 min. The reaction was stopped by addition of 20 uL 10× Stopping buffer (100 mM Tris-HCl, pH 8.0, 25 mM MgCl$_2$, 100 mM NaCl, 20 mM GTP).

For PTX treated samples, 100 μg of extract was brought up to 100 μL in GTPγS solublization/extraction buffer and treated with 500 ng/mL activated PTX in the presence of PTX Buffer (20 mM HEPES pH 8.0, 1 mM EDTA, 2 mM MgCl$_2$, 1 mM NAD). The sample was incubated for 12 hrs at 30° C. The PTX treated sample was then mixed with an equal volume of GTPγS Buffer B and taken through [$^{35}$S]GTPγS assay as described above.

Extracts of mouse frontal cortex were immunoprecipitated with a mixture of polyclonal antibodies to PS-1 and PS-2 (10 uL each) at 4° C. overnight to deplete the samples of PS-1 and PS-2. Protein A agarose (20 uL slurry/100 μg protein) was added and samples were and shaken end-over-end at 4° C. for 2 h. The PS-antibody-protein A complex was centrifuged at high speed for 5 min. Supernatant was recovered in and 100 μg aliquots were taken through the [$^{35}$S] GTPγS assay as described.

Following the GTPγS reaction, 5 uL of either anti-PS-1 or anti-PS-2 monoclonal antibodies were added and samples were placed at 4° C. overnight. The antibody-protein complex was bound to 20 μL Protein A/G agarose (Pharmacia) and samples were placed at 4° C. and shaken end-over-end for 2 hrs. The agarose beads were washed three times with Wash Buffer 1 (50 mM HEPES, pH 7.4, 1 mM EDTA, pH 8.0, 1% Triton-X100, 1× protease inhibitor mix) and once with each Wash Buffer 2(50 mM HEPES, pH 7.4, 1 mM EDTA, pH 8.0, 0.5% Triton-X100, 1× protease inhibitor mix) and 3(50 mM HEPES, pH 7.4, 1 mM EDTA, pH 8.0, 1× protease inhibitor mix). The washed agarose beads were then suspended in 5 mLs scintillation fluid (CytoScint, ICN) and counted on a Beckman Coulter LS 6000 SC scintillation counter for 3 min.

Figure 12:
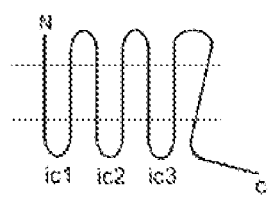
FIG. 12 illustrates intracellular domains of PS.

FIG. 12 shows the $^{35}$S-GTPγS incorporation in extracts of mouse brain that could be immunoprecipitated with monoclonal antibodies to PS-1, suggesting the co-precipitation of $^{35}$S-GTPγS-bound G-protein with the endogenous PS-1. This incorporation was greater than 80% of that found for extracts which had been prior depleted of PS-1 and PS-2 by treatment with polyclonal antibodies to the two PS proteins, showing specificity of the G-protein:PS-1 binding. Treatment with PTx inhibited the $^{35}$S-GTPγS incorporation by 60%.

Figure 13:
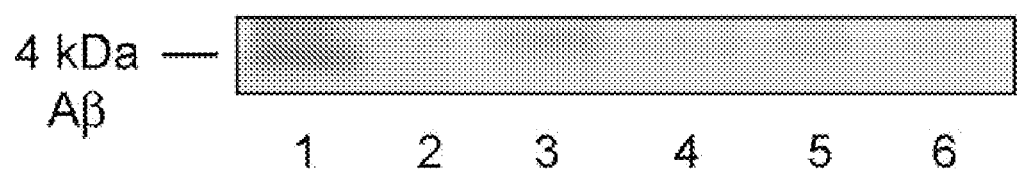
FIG. 13 shows the effect of intercellular β-APP:PS interactions on Aβ production.

FIG. 13 shows the $^{35}$S-GTPγS incorporation in extracts of mouse brain that could be immunoprecipitated with monoclonal antibodies to PS-2, suggesting the co-precipitation of $^{35}$S-GTPγS-bound G-protein with the endogenous PS-2. This incorporation was greater than 85% of that found for extracts which had been prior depleted of PS-1 and PS-2 by treatment with polyclonal antibodies to the two PS proteins, showing specificity of the G-protein:PS-2 binding. Treatment with PTx inhibited the $^{35}$S-GTPγS incorporation by 55%. These results demonstrate a specific PTx-sensitive G-protein coupling to endogenous mouse brain PS-1 and PS-2.

Sequences corresponding to the first 16 amino acids of intracellular loop 1 [ic1(1-16)], the remaining 16 amino acids of intracellular loop 1 [ic1(17-32)], the entire intracellular loop 2 (ic2), the entire intra-cellular loop 3 (ic3), the first 20 amino acids of the cytoplasmic C-terminal tail (C1-20) and the remaining 19 amino acids of the cytoplasmic C-terminal tail (C21-39) for both PS-1 and PS-2 will be synthesized and HPLC purified to >90% purity. FIG. 14 illustrates intracellular domains of PS. Table 1 shows the sequences that can be synthesized from these domains. In addition, a 20 amino acid control peptide synthesized in which the sequences of peptide C1-20 can be scrambled. This peptide is part of the 39 amino-acid sequence identified as the binding domain on PS-1 for G$_o$.

TABLE 1

| | PS-1 Cytoplasmic peptides | PS-2 Cytoplasmic peptides |
|---|---|---|
| ic1(1-16) | KSVSFYTRKDGQLIYT (SEQ ID NO: 7) | KSVRFYTEKNGQLIYT (SEQ ID NO: 12) |
| ic1(17-32) | PFTEDTETVGQRALHS (SEQ ID NO: 8) | TFTEDTPSVGQRLLNS (SEQ ID NO: 13) |
| ic2 | VFKTYNVAVD (SEQ ID NO: 9) | EVLKTYNVAMD (SEQ ID NO:14) |
| ic3 | MALVFIKYLPE (SEQ ID NO: 10) | (identical to ic3 of PS-1) |
| C(1-20) | KKALPALPISITFGLVFYFA (SEQ ID NO: 11) | KKALPALPISITFGLIFYFS (SEQ ID NO: 15) |
| C(21-39) | TDYLVQPFMDQLAFHQFYI (SEQ ID NO: 16)) | TDNLVRPFMDTLASHQLYI (SEQ ID NO: 17) |

Example 4

The present studies demonstrate that the GPCR function of PS-1 modulates the production of Aβ. A major question in the study of PS-GPCR function is to determine a specific ligand for PS that can elicit G-protein activities from the PS, to which the ligand binds intercellularly. The present studies investigated whether the three-part ligand-receptor-G-protein system initiates the production of Aβ. In such a system activation of PS by ligand (β-APP) binding would lead to G-protein binding to PS in the cytoplasmic domain.

In order to investigate whether G-protein binding to PS-1 or PS-2 affects Aβ production from β-APP, cell:cell interaction of β-APP and PS-1 in the presence and absence of Pertussis toxin (PTx) experiments were performed. PTx is a specific inhibitor of G-protein G$_o$ activation. If the GPCR function of PS is involved in the production of Aβ from β-APP:PS intercellular binding, then in its presence, Aβ production should be inhibited.

β-APP:PS-1 mediated cell-cell interactions were carried out using methods described above, with PS-1 transfected primary fibroblasts from β-APP-/- mice (cells express PS-1 and do not produce β-APP) interacted with β-APP-transfected ES (PS-/-) cells (cells produce β-APP but do not express PS) in the presence of $^{35}$S-methionine. 24 h after co-culture of the transfected cells, the samples were harvested in the presence of protease inhibitors. Cells were sonicated and 100 μg of whole cell extracts were immunoprecipitated with antibodies to Aβ (6E10) and immunoprecipitated samples were run on Bicene-Tris gels. Aβ bands were visualized by autoradiography of dried gels. The same experiment was carried out in the presence of 500 ng/ml of PTx. Treatment of cultured cells was carried out for 12 h as described below. As a control for PTX treatment, the cultured cells were incubated with PTx buffer only containing ATP and NAD. Under these conditions activation of Go and levels of Aβ should be unaffected.

FIG. 15 shows the results of these studies. Lane 1 shows the results of β-APP-expressing ES (PS-/-) cells co-cultured with PS-1-expressing Fibroblasts (β-APP-/-). Lane 2 shows the results of the components used in lane 1 in the presence of PTx and PTX buffer (NAD+ATP). Lane 3 shows the results of the components used in lane 1 in the presence of PTx buffer only (NAD+ATP), and no PTx. Lane 4 shows the results of tail-less β-APP-expressing ES (PS-/-) cells co-cultured with +Tail-less PS-1-expressing Fibroblasts (β-APP-/-). Lane 5 shows the results of the components used in lane 4 in the presence of PTx. Lane 6 shows the results of wild type β-APP-expressing ES (PS−/−) cells co-cultured with Tail-less PS-1-expressing fibroblasts (β-APP−/−).

The results indicate that PTx toxin inhibits the production of Aβ from the intercellular interaction of β-APP and PS-1 (lanes 1 and 2 above). Lane 3 shows that in the presence of PTx buffer only, but in the absence of PTx, Aβ production is not inhibited. Lanes 4 and 6 show that the cytoplasmic carboxyl terminal domain of PS-1, earlier shown to be the binding domain of PS-1 for Go, when absent, eliminates Aβ production.

The data provided herein indicate that β-APP is a ligand for PS-1 which upon binding activates its GPCR activity. The data also indicates that the GPCR function of PS-1 is involved in the production of Aβ from β-APP after its intercellular interaction with PS-1. These results further indicate that modulating GPCR activity of PS-1 also modulates the production of Aβ. Accordingly, agents that modulate GPCR activity of PS-1 will modulate the production of Aβ.

For co-culture experiments ES (PS$^{−/−}$) and β-APP($^{−/−}$) cells were plated at 1×10$^7$ cells per 25 cm$^2$ flask and transfected with the appropriate cDNAs. 5 hours after transfection, ES (PS-1$^{−/−}$/PS-2$^{−/−}$) cells transfected with β-APP were detached by mild trypsinization, washed 2× with met-free culture medium containing heat-inactivated, dialysed FCS (10% v/v) and resuspended in this medium at 0.33×10$^7$ cells/ml. Similarly, primary fibroblasts from β-APP knockout mice were co-transfected with PS-1 or PS-2 and plated at 1×10$^7$ cells. Transfected cells were washed 2× with met free medium and left in 3 ml met-free medium.

β-APP transfected ES (PS-1$^{−/−}$/PS-2$^{−/−}$) cells (1×10$^7$ cells/3 ml met-free medium) were added to the PS-1-transfected β-APP knockout cells. The cell densities ensured that essentially all the cells were in contact with another. $^{35}$S-met (66 µCi/ml; 1175 Ci/mmol, NEN) was added and the cultures incubated for 24 h. In experiments with PTx treatment, 500 ng/ml PTx was added to the cultures under the appropriate reaction conditions at this stage and incubated for 24 h. The medium was then removed and cells harvested by scraping. A protease inhibitor mix was added to the medium before freezing on dry ice. 100 µl extraction buffer (50 mM Tris, pH 8.0/150 mM NaCl/0.5% Nonidet-P40) containing protease inhibitors (1 mM 4-(2-aminoethyl)benzene sulfonyl fluoride hydrochloride (AEBSF)/1 µg/ml antipain/0.1 µg/ml pepstatin A/0.1 µg/ml leupeptin) was added to the cell pellet and the samples quick-frozen on dry ice.

The PTx protomer (Biomol Research Laboratories) was incubated with 10 mM DTT at 37° C. for 10 min to convert it to its enzymatically active form. 5 h after transfecting ES cells with PS-1 or PS-2 and the G-protein cDNAs, 500 ng/ml of activated PTx was added to the cells in culture medium in the presence of 1 mM NAD, 1 mM ATP, 2 mM MgCl2 and 1 mM EDTA. The cells were incubated at 37° C. in the presence of 5% CO$_2$ for 18 h.

Whole cell extracts were prepared using cell-pellets sonicated with 3 bursts of 20 seconds each on ice. Protein concentration was determined according to the method of Lowry.

Immunoprecipitations were carried out using 100 µg of cell extract subjected to immunoprecipitation in an end-over-end rotator at 4° C. overnight with 2 µg Aβ specific monoclonal antibodies 6E10 (Senetek), which was raised to residues 1-17 of Aβ (Senetek). 40 µl slurry of Protein G sepharose (Pharmacia) was then added and allowed to mix end-over-end for 1 h at room temperature. The antigen-antibody-Protein G sepharose complex was washed once with each of the following: buffer 1(10 mM Tris-HCl, pH 7.4, 1 mM EDTA, pH 8.0, 0.65M NaCL, 1% NP-40), buffer 2(10 mM Tris-HCl, pH 7.4, 1 mM EDTA, pH 8.0, 0.75% NP-40) and buffer 3(10 mM Tris-HCl, pH 7.4, 1 mM EDTA, pH 8.0, 0.1% NP-40). The washed complex was boiled for 10 min in bicene-tris sample buffer and subjected to SDS PAGE on bicene-tris gels.

Bicene-tris gels (15% T/5% C) with 8M urea was cast and run. The gels were then fixed for 30 min with 5% glutaraldehyde in 0.4M sodium borate/phosphate buffer and stained for 1 h with 0.1% Coomassie Blue G250 in methanol-acetic acid. After destaining the gels were prepared for autoradiography.

The destained gels were treated with ethanol (30%) and glycerol (5%) for 30 min and impregnated with Amplify (Amersham) for 30 min, dried under vacuum at 80° C. and exposed to X-Omat film at −70° C. for 4-5 days.

Although a number of embodiments and features have been described above, it will be understood by those skilled in the art that modifications and variations of the described embodiments and features may be made without departing from the teachings of the disclosure or the scope of the invention as defined by the appended claims. The appendices attached hereto are provided to further illustrate but not limit the invention.

What is claimed is:

1. A method of inhibiting Aβ production in a cell comprising:
    exposing cells to a peptide comprising an N-terminal domain of Presenilin-1, thereby inhibiting the binding of the N-terminal extracellular domain of βAPP with the N-terminal extracellular region of PS-1 and PS-2, or PS-1 or PS-2 and thereby inhibiting Aβ.

2. The method of claim 1, wherein the peptide is a soluble N-terminal domain of PS-1.

3. The method of claim 1, wherein the peptide is formulated with a pharmaceutically acceptable carrier.

4. A method of inhibiting Aβ production in a cell comprising contacting a cell with a peptide comprising an N-terminal soluble domain of Presenilin-1, wherein the peptide inhibits the interaction of βAPP with Presenilin-1, and thereby inhibiting Aβ production.

5. The method of claim 4, wherein the peptide inhibits a G-protein coupled receptor activity of presenilin-1.

6. The method of claim 4, wherein the peptide is formulated with a pharmaceutically acceptable carrier.

* * * * *

SEQUENCE LISTING

<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: Peptide Fragment of Presenilin-1 Homo sapiens

<400> SEQUENCE: 1

Lys Tyr Leu Pro Glu Trp
1               5

<210> SEQ ID NO 2
<211> LENGTH: 4
<212> TYPE: PRT
<213> ORGANISM: Artificial Sequence
<220> FEATURE:

-continued

```
<223> OTHER INFORMATION: Consensus sequence
<220> FEATURE:
<221> NAME/KEY: Misc
<222> LOCATION: (2)..(2)
<223> OTHER INFORMATION: Xaa can be any amino acid
<220> FEATURE:
<221> NAME/KEY: Misc
<222> LOCATION: (3)..(3)
<223> OTHER INFORMATION: Xaa can be any amino acid

<400> SEQUENCE: 2

Pro Xaa Xaa Pro
1

<210> SEQ ID NO 3
<211> LENGTH: 7
<212> TYPE: PRT
<213> ORGANISM: Artificial Sequence
<220> FEATURE:
<223> OTHER INFORMATION: Consensus Sequence
<220> FEATURE:
<221> NAME/KEY: Misc
<222> LOCATION: (2)..(2)
<223> OTHER INFORMATION: Xaa is any amino aicd
<220> FEATURE:
<221> NAME/KEY: Misc
<222> LOCATION: (5)..(5)
<223> OTHER INFORMATION: Xaa is any amino acid
<220> FEATURE:
<221> NAME/KEY: Misc
<222> LOCATION: (6)..(6)
<223> OTHER INFORMATION: Xaa is a hydrophobic amino acid or Arginine
      residue

<400> SEQUENCE: 3

Arg Xaa Leu Pro Xaa Xaa Pro
1               5

<210> SEQ ID NO 4
<211> LENGTH: 13
<212> TYPE: PRT
<213> ORGANISM: Artificial Sequence
<220> FEATURE:
<223> OTHER INFORMATION: Consensus Sequence of peptide substrate for Src

<400> SEQUENCE: 4

Lys Val Glu Lys Ile Gly Thr Tyr Gly Val Val Lys Lys
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Consensus Sequence of peptide substrate for Src

<400> SEQUENCE: 5

Lys Val Glu Lys Ile Gly Val Gly Ser Tyr Gly Val Val Lys Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Consensus Sequence of Peptide substrate for Src

<400> SEQUENCE: 6

Lys Val Glu Lys Ile Gly Glu Gly Thr Phe Gly Val Val Lys Lys
1               5                   10                  15
```

```
<210> SEQ ID NO 7
<211> LENGTH: 16
<212> TYPE: PRT
<213> ORGANISM: Homo sapiens

<400> SEQUENCE: 7

Lys Ser Val Ser Phe Tyr Thr Arg Lys Asp Gly Gln Leu Ile Tyr Thr
1               5                   10                  15

<210> SEQ ID NO 8
<211> LENGTH: 16
<212> TYPE: PRT
<213> ORGANISM: Homo sapiens

<400> SEQUENCE: 8

Pro Phe Thr Glu Asp Thr Glu Thr Val Gly Gln Arg Ala Leu His Ser
1               5                   10                  15

<210> SEQ ID NO 9
<211> LENGTH: 10
<212> TYPE: PRT
<213> ORGANISM: Homo sapiens

<400> SEQUENCE: 9

Val Phe Lys Thr Tyr Asn Val Ala Val Asp
1               5                   10

<210> SEQ ID NO 10
<211> LENGTH: 11
<212> TYPE: PRT
<213> ORGANISM: Homo sapiens

<400> SEQUENCE: 10

Met Ala Leu Val Phe Ile Lys Tyr Leu Pro Glu
1               5                   10

<210> SEQ ID NO 11
<211> LENGTH: 20
<212> TYPE: PRT
<213> ORGANISM: Homo sapiens

<400> SEQUENCE: 11

Lys Lys Ala Leu Pro Ala Leu Pro Ile Ser Ile Thr Phe Gly Leu Val
1               5                   10                  15

Phe Tyr Phe Ala
            20

<210> SEQ ID NO 12
<211> LENGTH: 16
<212> TYPE: PRT
<213> ORGANISM: Homo sapiens

<400> SEQUENCE: 12

Lys Ser Val Arg Phe Tyr Thr Glu Lys Asn Gly Gln Leu Ile Tyr Thr
1               5                   10                  15

<210> SEQ ID NO 13
<211> LENGTH: 16
<212> TYPE: PRT
<213> ORGANISM: Homo sapiens

<400> SEQUENCE: 13

Thr Phe Thr Glu Asp Thr Pro Ser Val Gly Gln Arg Leu Leu Asn Ser
1               5                   10                  15
```

```
<210> SEQ ID NO 14
<211> LENGTH: 11
<212> TYPE: PRT
<213> ORGANISM: Homo sapiens

<400> SEQUENCE: 14

Glu Val Leu Lys Thr Tyr Asn Val Ala Met Asp
1               5                   10

<210> SEQ ID NO 15
<211> LENGTH: 20
<212> TYPE: PRT
<213> ORGANISM: Homo sapiens

<400> SEQUENCE: 15

Lys Lys Ala Leu Pro Ala Leu Pro Ile Ser Ile Thr Phe Gly Leu Thr
1               5                   10                  15

Phe Tyr Phe Ser
            20

<210> SEQ ID NO 16
<211> LENGTH: 19
<212> TYPE: PRT
<213> ORGANISM: Homo sapiens

<400> SEQUENCE: 16

Thr Asp Tyr Leu Val Gln Pro Phe Met Asp Gln Leu Ala Phe His Gln
1               5                   10                  15

Phe Tyr Ile

<210> SEQ ID NO 17
<211> LENGTH: 19
<212> TYPE: PRT
<213> ORGANISM: Homo sapiens

<400> SEQUENCE: 17

Thr Asp Asn Leu Val Arg Pro Phe Met Asp Thr Leu Ala Ser His Gln
1               5                   10                  15

Leu Tyr Ile
```